United States Patent
Gomi et al.

(10) Patent No.: US 8,106,053 B2
(45) Date of Patent: Jan. 31, 2012

(54) 5-PHENYL-3-PYRIDAZINONE DERIVATIVE

(75) Inventors: Noriaki Gomi, Higashimurayama (JP); Shinji Ina, Higashimurayama (JP); Kenjirou Yamana, Higashimurayama (JP); Yoshio Kaneko, Higashimurayama (JP)

(73) Assignee: Kowa Company, Ltd., Nagoya, JPX ( * ) Notice: Subject to any disclaimer, the term of this patent is extended or adjusted under 35 U.S.C. 154(b) by 0 days.

(21) Appl. No.: 12/665,492

(22) PCT Filed: Jun. 19, 2008

(86) PCT No.: PCT/JP2008/061596
§ 371 (c)(1),
(2), (4) Date: Dec. 18, 2009

(87) PCT Pub. No.: WO2008/156208
PCT Pub. Date: Dec. 24, 2008

(65) Prior Publication Data
US 2010/0197698 A1    Aug. 5, 2010

(30) Foreign Application Priority Data
Jun. 20, 2007    (JP) ................................. 2007-163176

(51) Int. Cl.
*A61K 31/50* (2006.01)
*A61K 31/501* (2006.01)
*C07D 237/02* (2006.01)

(52) U.S. Cl. .................................. 514/252.01; 544/224

(58) Field of Classification Search .................. 544/224; 514/252.01
See application file for complete search history.

(56) References Cited

U.S. PATENT DOCUMENTS

| | | |
|---|---|---|
| 4,678,786 A | 7/1987 | Roe et al. |
| 4,820,819 A | 4/1989 | Roe et al. |
| 6,235,739 B1 * | 5/2001 | Ina et al. ........................ 514/247 |
| 7,569,518 B2 | 8/2009 | Morishita et al. |

FOREIGN PATENT DOCUMENTS

| | | |
|---|---|---|
| JP | 60-89421 A | 5/1985 |
| JP | 10-59950 A | 3/1998 |
| WO | WO-2005/121104 A1 | 12/2005 |

OTHER PUBLICATIONS

Vippagunta et al., "Crystalline Solids", Adv. Drug Del. Rev., 48 (2001) 3-26.*
International Search Report for PCT/JP2008/061596 dated Oct. 22, 2009.
Nikken Chem Co Ltd., "5-Phnyl-3-Pyridazinone Derivative," Patent Abstracts of Japan, Publication No. 10059950-A, English Abstract for JP10-59950.

* cited by examiner

Primary Examiner — Paul V. Ward
(74) Attorney, Agent, or Firm — Millen, White, Zelano & Branigan, P.C.

(57) ABSTRACT

To find a compound having a tissue fibrinosis-inhibitory activity and a fibrinolytic activity, and to provide a novel compound that is useful for preventing and/or treating tissue fibrinosis diseases (pulmonary fibrosis, renal fibrosis etc.), diseases caused by pathological blood clots such as ischemic heart diseases (myocardial infarction, angina), intraatrial thrombus, pulmonary embolism, deep venous thrombosis, disseminated intravascular coagulation, ischemic cerebral diseases (cerebral infarction, cerebral bleeding) and arteriosclerosis and the like. To provide a pharmaceutical drug comprising a 5-phenyl-3-pyridazinone derivative represented by the following general formula (I):

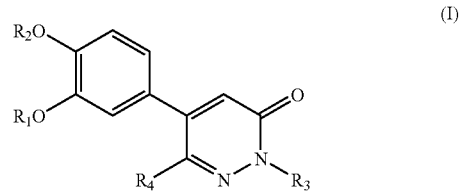

and an optical isomer thereof, or a pharmaceutically acceptable salt thereof, or a hydrate or solvate thereof, useful for preventing and/or treating disease conditions or symptoms mediated by plasminogen activator inhibitor-1.

8 Claims, No Drawings

5-PHENYL-3-PYRIDAZINONE DERIVATIVE

FIELD OF THE INVENTION

The present invention relates to a 5-phenyl-3-pyridazinone derivative having an inhibitory activity of the production of plasminogen activator inhibitor-1 (hereinafter referred to as PAI-1).

BACKGROUND ART

Clot formation is an important biological reaction that forms hemostatic plugs to stop bleeding in normal processes. However, abnormal clot formation is thought to be responsible for ischemic diseases that are considered to be a major cause of death in Japan and western countries. Many diseases are caused by pathological blood clots, and those reported include, for example, ischemic heart diseases (myocardial infarction, angina), intraatrial thrombus, pulmonary embolism, deep venous thrombosis, disseminated intravascular coagulation, ischemic cerebral diseases (cerebral infarction, cerebral bleeding) and arteriosclerosis. Currently, a number of medicaments are being used for these pathological blood clots. As representative medicaments, there can be mentioned anti-platelet agents, inhibitors of blood coagulation factors, vitamin K inhibitors and fibrinolytic agents.

The activation of the fibrinolytic system is triggered by the activation of plasminogen by plasminogen activators t-PA and urokinase to plasmin, and the formed plasmin decomposes fibrin, a constituent of blood clots, to allow thrombolysis to proceed. Among them, a physiological control factor for plasminogen activator is PAI-1 that is released from vascular endothelial cells or the activated platelets. PAI-1 is composed of 379 amino acids, and is a glycoprotein with a molecular weight of about 50 kDa having no intramolecular S—S bonds. PAI-1 binds to the enzymatic active center of t-PA at a molar ratio of 1:1, and inhibits the t-PA activity. Under normal conditions, fibrinolytic control factors keep equilibrium with each other causing no bleeding or clotting to attain smooth blood flow in the blood vessel. However, it is thought that in pathological thrombosis and vascular endothelial cells, t-PA production is reduced whereas PAI-1 secretion is increased. Thus, it is thought that by inhibiting PAI-1 that is increased in pathological thrombosis, a therapeutic effect may be exhibited.

On the other hand, pathological conditions in which fibrin is involved is not limited to thrombosis, and it is known that fibrin clots are massively formed in tissue fibrinosis as well. Though fibrinosis is a pathological condition that is observed in various organs including the lung, the kidney, the liver, the skin, cerebral nerves, blood vessels and the like, the pathological causes have not been elucidated much less the therapeutic methods. There are reports on bleomycin-induced pulmonary fibrosis which is an animal model of fibrinosis. It has been reported that in PAI-1 knockout mice, the enhancement in the amount of hydroxyproline that is an index of fibrinolysis is inhibited, and in mice over-expressing PAI-1 the production of hydroxyproline is increased compared to the control (J. Clin. Invest. 97, 232 (1996)). It is also reported that by administering uPA that is increased by inhibiting PAI-1, the formed fibrins can be dissolved (Clin. Invest. Med., 17: 69-76 (1994)). These suggest that the inhibition of PAI-1 may lead to a therapeutic effect for fibrinolysis.

So far, compounds that inhibit PAI-1 are known (Kokai (Japanese Unexamined Patent Publication) No. 7-149642, Kokai No. 7-149643, Kokai No. 7-165573, Kokai No. 7-165574, Kokai No. 10-287622, Kokai No. 2003-89687, Kokai No. 2004-203793, European Patent Publication No. 0563798, the International Patent Publication WO 95/32190 brochure, the International Patent Publication WO 03/000684 brochure), but they have not been clinically applied, and further development of useful compounds are being sought after.

Kokai (Japanese Unexamined Patent Publication) No. 60-89421 describes a compound represented by the following general formula (II) as a beta-adrenalin receptor antagonist:

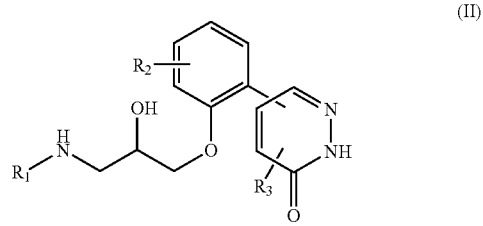

(II)

wherein, $R_1$ represents an isopropyl group or a t-butyl group, $R_2$ represents a hydrogen atom, a $C_1$-$C_4$ alkyl group, a $C_1$-$C_4$ alkoxy group, a hydroxy group or an amino group, and $R_3$ represents a hydrogen atom or a methyl group. The above compound has a structural similarity with the compound of the present invention in terms of being a phenylpyridazine derivative. However, it differs greatly in that it has a substituent at position 2 of the phenyl group whereas the compound of the present invention is characterized by being a pyridazinone derivative having as a substituent a phenyl group that has an alkoxy group at positions 3 and 4. Furthermore, it is neither mentioned nor known that these derivatives (II) have an inhibitory activity of PAI-1 production. Kokai (Japanese Unexamined Patent Publication) No. 10-59950 describes that a compound having the following general formula (III):

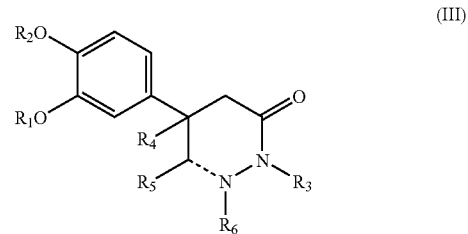

(III)

[wherein, $R_1$ represents a $C_1$-$C_4$ alkyl group, a $C_3$-$C_7$ cycloalkyl group or the like, $R_2$ represents a $C_1$-$C_4$ alkyl group, $R_3$ represents a hydrogen atom, an optionally substituted $C_1$-$C_5$ alkyl group, $C_3$-$C_7$ cycloalkyl group or the like, and $R_4$ and $R_5$ represent a hydrogen atom, a $C_1$-$C_6$ alkyl group or the like, and the dotted line represents a single or double bond] has a potent PDE IV inhibiting activity, and bronchodilating and antiinflammatory activities. The above derivative (III) has a structural similarity with the compound of the present invention in terms of being a 5-dialkoxyphenyl-3-pyridazinone, but it differs greatly in that the bond between positions 4 and 5 of the pyridazinone ring is a single bond. Also, it is neither mentioned nor known that the above derivative (III) has an activity of inhibiting PAI-1 production. International Patent Publication WO 05/077953 describes a compound represented by the following general formula (IV):

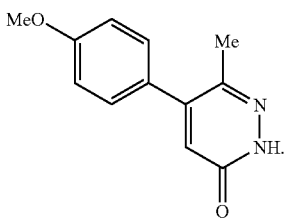

(IV)

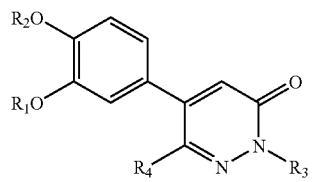

(I)

The above derivative (IV) has a structural similarity with the compound of the present invention in terms of being a 5-phenyl-3-pyridazinone, but it differs greatly in that it has no alkoxy group at position 3 of the benzene ring or it is not a 5-dialkoxyphenyl-3-pyridazinone. Also, it is neither mentioned nor known that the above derivative (IV) has an activity of inhibiting PAI-1 production. International Patent Publication WO 05/121104 describes that a compound represented by the following general formula (V):

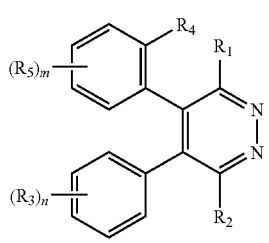

(V)

has an efficacy of combating plant diseases. The above derivative (IV) differs greatly with the compound of the present invention in that it has two phenyl groups on the pyridazinone ring. Also, it is neither mentioned nor known that the above derivative (V) has an activity of inhibiting PAI-1 production.

DISCLOSURE OF THE INVENTION

It is an object of the present invention to provide a compound having a PAI-1 production-inhibiting activity, a tissue fibrosis-inhibiting activity, and a fibrinolytic activity. it is also an object of the present invention to provide a pharmaceutical drug for the prevention and/or treatment of diseases caused by pathological blood clots such as ischemic heart diseases (myocardial infarction, angina), intraatrial thrombus, pulmonary embolism, deep venous thrombosis, disseminated intravascular coagulation, ischemic cerebral diseases (cerebral infarction, cerebral bleeding) and arteriosclerosis.

As a result of exploring compounds having an inhibitory activity of PAI-1 production, it was found that a 5-phenyl-3-pyridazinone derivative of the present invention has a potent PAI-1 production-inhibiting activity, a potent tissue fibrosis-inhibiting activity, and a potent fibrinolytic activity, and therefore the present invention has been completed. Thus, the summary of the present invention is a 5-phenyl-3-pyridazinone derivative represented by the following general formula (I):

[wherein, $R_1$ represents a $C_1$-$C_8$ alkyl group optionally having one or more than one substituent (a halogen atom; a hydroxy group; a nitro group; a cyano group; an amino group; a carboxyl group; an alkyl group; a cycloalkyl group optionally having one or more than one phenyl group or alkyl group; a haloalkyl group; a carbamoyl group optionally having one or more than one alkyl group on the nitrogen atom; an alkoxy group; an alkoxycarbonyl group; an acyl group; a monocyclic or fused polycyclic aryl group; a monocyclic or fused polycyclic heterocyclic group having one or more than one heteroatom), a $C_3$-$C_7$ cycloalkyl group optionally having one or more than one of the above substituents, a 3-7-membered monocyclic nonaromatic heterocyclic group containing one or more than one heteroatom that may have one or more than one of the above substituents, or an indanyl group, $R_2$ represents a $C_1$-$C_4$ alkyl group or a $C_1$-$C_4$ haloalkyl group, and $R_3$ represents a hydrogen atom, a $C_1$-$C_8$ alkyl group optionally having one or more than one substituent (a halogen atom; a hydroxy group; a nitro group; a cyano group; an amino group; a carboxyl group; an alkyl group; a cycloalkyl group optionally having one or more than one phenyl group or alkyl group; a haloalkyl group; a carbamoyl group optionally having one or more than one alkyl group on the nitrogen atom; an alkoxy group; an alkoxycarbonyl group; an acyl group; a monocyclic or fused polycyclic aryl group; a monocyclic or fused polycyclic heterocyclic group having one or more than one heteroatom), a $C_3$-$C_7$ cycloalkyl group, a 3-7-membered monocyclic nonaromatic heterocyclic group containing one or more than one heteroatom, a monocyclic or fused polycyclic aryl group, or a monocyclic or fused polycyclic heteroaryl group having one or more than one heteroatom, and $R_4$ represents a hydrogen atom or a $C_1$-$C_6$ alkyl group], and an optical isomer thereof, or a pharmaceutically acceptable salt thereof, or a hydrate or solvate thereof.

The compound of the present invention has an excellent inhibitory activity of plasminogen activator inhibitor-1 production, and, due to its fibrinolytic activity, is useful as a pharmaceutical drug for prevention and/or treating tissue fibrinosis diseases such as pulmonary fibrosis and renal fibrosis, diseases caused by pathological blood clots such as ischemic heart diseases (myocardial infarction, angina), intraatrial thrombus, pulmonary embolism and deep venous thrombosis and the like.

BEST MODE FOR CARRYING OUT THE INVENTION $R_1$ of the above general formula (I) represents a $C_1$-$C_8$ alkyl group optionally having one or more than one substituent, a $C_3$-$C_7$ cycloalkyl group optionally having one or more than one substituent, or a 3-7-membered monocyclic nonaromatic heterocyclic group optionally having one or more than one heteroatom containing one or more than one substituent, or an indanyl group.

As a "substituent" in "a $C_1$-$C_8$ alkyl group optionally having one or more than one substituent", "a $C_3$-$C_7$ cycloalkyl group optionally having one or more than one substituent", or "a 3-7-membered monocyclic nonaromatic heterocyclic group containing one or more than one heteroatom optionally having one or more than one substituent" represented by $R_1$, there can be mentioned a halogen atom (for example, fluorine; chlorine; bromine; iodine), a hydroxy group, a nitro group, a cyano group, an amino group, a carboxyl group, a $C_1$-$C_6$ alkyl group, a $C_3$-$C_7$ cycloalkyl group optionally having a substituent (a phenyl group or a $C_1$-$C_6$ alkyl group), a $C_1$-$C_6$ haloalkyl group, a carbamoyl group optionally having one or more than one $C_1$-$C_4$ alkyl group as a substituent on the nitrogen atom, a $C_1$-$C_6$ alkoxy group, a $C_1$-$C_6$ alkoxycarbonyl group, a $C_1$-$C_6$ acyl group, a 6-10-membered monocyclic or a fused polycyclic aryl group, a monocyclic or fused polycyclic heterocyclic group having one or more than one heteroatom (for example, a 3-10-membered monocyclic or fused polycyclic nonaromatic heterocyclic group containing one or more than one heteroatom, or a 5-10-membered monocyclic or fused polycyclic heteroaryl group containing one or more than one heteroatom), and the like.

As $R_1$, there can be preferably mentioned a $C_1$-$C_8$ alkyl group, a $C_1$-$C_5$ alkyl group having one or more than one phenyl group or a furyl group as a substituent, a $C_1$-$C_5$ alkyl group having as a substituent one or more than one $C_3$-$C_7$ cycloalkyl group optionally having as a substituent one or more than one phenyl group or a $C_1$-$C_3$ alkyl group, a $C_4$-$C_6$ cycloalkyl group optionally having one or more than one substituent group (a methyl group; a hydroxy group etc.), a phenyl group, and a 5-6-membered nonaromatic heterocyclic group or an indanyl group containing one or more than one heteroatom optionally having one or more than one substituent group (a methyl group; a hydroxy group etc.), and as $R_1$, a methyl group, an ethyl group, a propyl group, a butyl group, an isobutyl group, a pentyl group, a neopentyl group, a 2-ethylbutyl group, a cyclopropylmethyl group, a cyclobutylmethyl group, a cyclopentylmethyl group, a cyclohexylmethyl group, a benzyl group, a phenetyl group, a 3-phenylpropyl group, a 4-phenylbutyl group, a (1-methylcyclopropyl)methyl group, a (1-phenylcyclopropyl)methyl group, a 2-furylmethyl group, a 2-furylethyl group, a 3-(2-furyl)propyl group, a cyclopentyl group, a 3-tetrahydrofuryl group or a 2-indanyl group etc. may be more preferred, and among them, a cyclopentyl group, a 3-tetrahydrofuryl group, a cyclopropylmethyl group and a 2-indanyl group may be mentioned as specifically preferred groups.

As $R_2$, a $C_1$-$C_4$ alkyl group and a $C_1$-$C_4$ haloalkyl group may be mentioned, and preferably a methyl group, an ethyl group, a trifluoromethyl group or a difluoromethyl group may be mentioned.

$R_3$ represents a hydrogen atom, a $C_1$-$C_5$ alkyl group optionally having one or more than one substituent, a $C_3$-$C_7$ cycloalkyl group, a 3-7-membered monocyclic nonaromatic heterocyclic group containing one or more than one heteroatom, a monocyclic or fused polycyclic aryl group (a 6-10-membered monocyclic or fused polycyclic aryl group), or a monocyclic or fused polycyclic heteroaryl group containing one or more than one heteroatom (a 5-10-membered monocyclic or fused polycyclic heteroaryl group).

As a "substituent" in "a $C_1$-$C_5$ alkyl group optionally having one or more than one substituent" represented by $R_3$, there can be mentioned a halogen atom (for example, fluorine; chlorine; bromine; iodine), a hydroxy group, a nitro group, a cyano group, an amino group, a carboxyl group, a $C_1$-$C_6$ alkyl group, a $C_3$-$C_7$ cycloalkyl group optionally having a substituent (a phenyl group or a $C_1$-$C_6$ alkyl group), a $C_1$-$C_6$ haloalkyl group, a carbamoyl group optionally having as a substituent one or more than one $C_1$-$C_4$ alkyl group on the nitrogen atom, a $C_1$-$C_6$ alkoxy group, a $C_1$-$C_6$ alkoxycarbonyl group, a $C_1$-$C_6$ acyl group, a 6-10-membered monocyclic or fused polycyclic aryl group, a monocyclic or fused polycyclic heterocyclic group containing one or more than one heteroatom (for example, a 3-10-membered monocyclic or fused polycyclic nonaromatic heterocyclic group containing one or more than one heteroatom or a 5-10-membered monocyclic or fused polycyclic heteroaryl group containing one or more than one heteroatom) etc.

As groups that may be substituted for the $C_1$-$C_5$ alkyl group in $R_3$, there can be preferably mentioned a $C_3$-$C_7$ cycloalkyl group, a phenyl group, a naphthyl group, a pyridyl group, a furyl group, a thiazolyl group, a quinolyl group and an oxobenzothiazolyl group etc.

As a $C_1$-$C_5$ alkyl group optionally having a substituent of $R_3$, there can be mentioned a benzyl group, a phenetyl group, a 3-phenylpropyl group, a 4-phenylbutyl group, a 5-phenylpentyl group, a pyridylmethyl group, a furylmethyl group, a thiazolylmethyl group, a 1-naphthylmethyl group, a quinolylmethyl group, a cyclopropylmethyl group, a cyclobutylmethyl group, a cyclopentylmethyl group, a cyclohexylmethyl group, a (1-methylcyclopropyl)methyl group, a (1-phenylcyclopropyl)methyl group, a 2-furylethyl group, oxobenzothiazolyl group etc.

As $R_3$, furthermore, there can be mentioned a $C_3$-$C_7$ cycloalkyl group (a cyclopropyl group; a cyclobutyl group; a cyclopentyl group; a cyclohexyl group; a cycloheptyl group etc.), a 6-10-membered monocyclic or fused polycyclic aryl group (a phenyl group; a naphthyl group etc.), and a 5-10-membered monocyclic or fused polycyclic heteroaryl group containing one or more than one heteroatom (a pyridyl group; a thiazolyl group; a furyl group; a thienyl group; a quinolyl group; an oxyranyl group; an aziridinyl group; a tetrahydrofuryl group etc.).

As $R_3$, there can be preferably mentioned a hydrogen atom, a $C_1$-$C_8$ alkyl group, a $C_3$-$C_7$ cycloalkyl group (a cyclopropyl group; a cyclobutyl group; a cyclopentyl group; a cyclohexyl group; a cycloheptyl group etc.), a 6-10-membered monocyclic or fused polycyclic aryl group, a 5-10-membered monocyclic or fused polycyclic heteroaryl group containing one or more than one heteroatom (a pyridyl group; a thiazolyl group; a furyl group; a thienyl group; a quinolyl group; an oxyranyl group; an aziridinyl group; a tetrahydrofuryl group etc.), a $C_1$-$C_2$ alkyl group having a substituent group (a phenyl group; a pyridyl group; a furyl group; a quinolyl group, an oxobenzothiazolinyl group etc.), and more preferably a hydrogen atom, a methyl group, an ethyl group, a 3-penyl group, a phenyl group, a cyclopentyl group, an oxyranyl group, a pyridyl group, a benzyl group, a 2-quinolylmethyl group, an oxobenzothiazolinylmethyl group may be mentioned. Among them, a hydrogen atom, a methyl group, a 3-penyl group, a 2-quinolylmethyl group, and a 2-oxobenzothiazolinyl-3-ylmethyl group are specifically preferred.

As $R_4$, there can be mentioned a hydrogen atom, a $C_1$-$C_6$ alkyl group (a methyl group; an ethyl group; a propyl group; an isopropyl group; a butyl group; a sec-butyl group; a tert-butyl group; a pentyl group; an isopentyl group; a neopentyl group; a hexyl group; an isohexyl group; a 2-ethylbutyl group; a 1-methylpropyl group; a 1,1-dimethylbutyl group; a 2,2-dimethylbutyl group; a 3,3-dimethylbutyl group etc.), and preferably a hydrogen atom and a methyl group may be mentioned.

In a further detailed explanation of the present invention:

(In the above general formula (I), $R_1$ represents a $C_1$-$C_8$ alkyl group (a methyl group; an ethyl group; a propyl group; an isopropyl group; a butyl group; a sec-butyl group; a tert-butyl group; a pentyl group; a hexyl group; an isopentyl group; a neopentyl group; a 1-methylpropyl group; an isohexyl group; a 1,1-dimethylbutyl group; a 2,2-dimethylbutyl group; a 3,3-dimethylbutyl group; a heptyl group or an octyl group etc.) optionally having one or more than one substituent group (fluorine; chlorine; bromine; iodine; a hydroxy group; a nitro group; a cyano group; an amino group; a carboxyl group; a methyl group; an ethyl group; a propyl group; a butyl group; a pentyl group; a hexyl group; an isopropyl group; a sec-butyl group; a tert-butyl group; an isopentyl group; a neopentyl group; a 1-methylpropyl group; an isohexyl group; a 1,1-dimethylbutyl group; a 2,2-dimethylbutyl group; a 3,3-dimethylbutyl group; a $C_3$-$C_7$ cycloalkyl group (a cyclopropyl group; a cyclobutyl group; a cyclopentyl group; a cyclohexyl group; a cycloheptyl group etc.) optionally having a substituent group (a phenyl group; a methyl group; an ethyl group; a propyl group; a butyl group; a pentyl group; a hexyl group; an isopropyl group; a sec-butyl group; a tert-butyl group; an isopentyl group; a neopentyl group; a 1-methylpropyl group; an isohexyl group; a 1,1-dimethylbutyl group; a 2,2-dimethylbutyl group; a 3,3-dimethylbutyl group etc.); a $C_1$-$C_6$ alkyl group (a methyl group; an ethyl group; a propyl group; a butyl group; a pentyl group; a hexyl group; an isopropyl group; a sec-butyl group; a tert-butyl group; an isopentyl group; a neopentyl group; a 1-methylpropyl group; an isohexyl group; a 1,1-dimethylbutyl group; a 2,2-dimethylbutyl group; a 3,3-dimethylbutyl group etc.) having one or more than one halogen atom (fluorine; chlorine; bromine; iodine); a carbamoyl group; a methylcarbamoyl group; an ethylcarbamoyl group; a propylcarbamoyl group; an isopropylcarbamoyl group; a butylcarbamoyl group; a sec-butylcarbamoyl group; a tert-butylcarbamoyl group; a dimethylcarbamoyl group; a diethylcarbamoyl group; a dipropylcarbamoyl group; a diisopropylcarbamoyl group; a dibutylcarbamoyl group; a di-sec-butylcarbamoyl group; a di-tert-butylcarbamoyl group; a N-ethyl-N-methylcarbamoyl group; a N-methyl-N-propylcarbamoyl group; a N-isopropyl-N-methylcarbamoyl group; a N-butyl-N-methylcarbamoyl group; a N-sec-butyl-N-methylcarbamoyl group; a N-tert-butyl-N-methylcarbamoyl group; a N-ethyl-N-propylcarbamoyl group; a N-ethyl-N-isopropylcarbamoyl group; a N-butyl-N-ethylcarbamoyl group; a N-sec-butyl-N-ethylcarbamoyl group; a N-tert-butyl-N-ethylcarbamoyl group; a N-isopropyl-N-propylcarbamoyl group; a N-butyl-N-propylcarbamoyl group; a N-sec-butyl-N-propylcarbamoyl group; a N-tert-butyl-N-propylcarbamoyl group; a N-butyl-N-isopropylcarbamoyl group; a N-sec-butyl-N-isopropylcarbamoyl group; a N-tert-butyl-N-isopropylcarbamoyl group; a N-butyl-N-sec-butylcarbamoyl group; a N-butyl-N-tert-butylcarbamoyl group; a N-sec-butyl-N-tert-butylcarbamoyl group; a methoxy group; an ethoxy group; a propoxy group; an isopropoxy group; a butoxy group; a sec-butoxy group; a tert-butoxy group; a pentyloxy group; a hexyloxy group; a methoxycarbonyl group; an ethoxycarbonyl group; a propoxycarbonyl group; an isopropoxycarbonyl group; a butoxycarbonyl group; a sec-butoxycarbonyl group; a tert-butoxycarbonyl group; a pentyloxycarbonyl group; a hexyloxycarbonyl group; a formyl group; an acetyl group; a propionyl group; a butyryl group; an isobutyryl group; a valeryl group; an isovaleryl group; a pivaloyl group; an acryloyl group; a propioyl group; a phenyl group; a naphthyl group; a 3-10-membered monocyclic or fused polycyclic nonaromatic heterocyclic group containing one or more than one heteroatom (an oxyranyl group; an aziridinyl group; an oxetanyl group; a thietanyl group; a thioranyl group; a thiomorpholinyl group; a pyrrolidinyl group; a pyrrolinyl group; an imidazolidinyl group; an imidazolinyl group; a tetrahydrofuryl group; a pyrazolidinyl group; a pyrazolinyl group; a pyranyl group; a tetrahydropyranyl group; a piperazinyl group; a morpholinyl group; a piperidinyl group; an indolinyl group; an isoindolinyl group; a dihydrobenzofuranyl group; an oxobenzothiazolinyl group etc.); a 5-10-membered monocyclic or fused polycyclic heteroaryl group containing one or more than one heteroatom (a thiazolyl group; a thienyl group; a furyl group; an isothiazolyl group; an oxazolyl group; an isoxazolyl group; a pyrrolyl group; a imidazolyl group; a furazanyl group; a pyrazolyl group; a pyridyl group; a pyrazinyl group; a pyrimidinyl group; a pyridazinyl group; a triazinyl group; a quinolyl group; an isoquinolyl group; an indolyl group; an isoindolyl group; an indolidinyl group; an indazolyl group; a phthalazinyl group; a naphthilidinyl group; a quinoxalinyl group; a quinazolinyl group; a prinyl group; a pteridinyl group; a synnolinyl group; a chromenyl group; a benzofuranyl group; a benzooxazolyl group; a benzisoxazolyl group; a benzothiazolyl group; a benzisothiazolyl group; a benzimidazolyl group etc.)), a $C_3$-$C_7$ cycloalkyl group (a cyclopropyl group; a cyclobutyl group; a cyclopentyl group; a cyclohexyl group; a cycloheptyl group) optionally having one or more than one substituent group (fluorine; chlorine; bromine; iodine; a hydroxy group; a nitro group; a cyano group; an amino group; a carboxyl group; a methyl group; an ethyl group; a propyl group; a butyl group; a pentyl group; a hexyl group; an isopropyl group; a sec-butyl group; a tert-butyl group; an isopentyl group; a neopentyl group; a 1-methylpropyl group; an isohexyl group; a 1,1-dimethylbutyl group; a 2,2-dimethylbutyl group; a 3,3-dimethylbutyl group; a $C_3$-$C_7$ cycloalkyl group (a cyclopropyl group; a cyclobutyl group; a cyclopentyl group; a cyclohexyl group; a cycloheptyl group etc.) optionally having a substituent group (a phenyl group; a methyl group; an ethyl group; a propyl group; a butyl group; a pentyl group; a hexyl group; an isopropyl group; a sec-butyl group; a tert-butyl group; an isopentyl group; a neopentyl group; a 1-methylpropyl group; an isohexyl group; a 1,1-dimethylbutyl group; a 2,2-dimethylbutyl group; a 3,3-dimethylbutyl group etc.); a $C_1$-$C_6$ alkyl group (a methyl group; an ethyl group; a propyl group; a butyl group; a pentyl group; a hexyl group; an isopropyl group; a sec-butyl group; a tert-butyl group; an isopentyl group; a neopentyl group; a 1-methylpropyl group; an isohexyl group; a 1,1-dimethylbutyl group; a 2,2-dimethylbutyl group; a 3,3-dimethylbutyl group etc.) having one or more than one halogen atom (fluorine; chlorine; bromine; iodine); a carbamoyl group; a methylcarbamoyl group; an ethylcarbamoyl group; a propylcarbamoyl group; an isopropylcarbamoyl group; a butylcarbamoyl group; a sec-butylcarbamoyl group; a tert-butylcarbamoyl group; a dimethylcarbamoyl group; a diethylcarbamoyl group; a dipropylcarbamoyl group; a diisopropylcarbamoyl group; a dibutylcarbamoyl group; a di-sec-butylcarbamoyl group; a di-tert-butylcarbamoyl group; a N-ethyl-N-methylcarbamoyl group; a N-methyl-N-propylcarbamoyl group; a N-isopropyl-N-methylcarbamoyl group; a N-butyl-N-methylcarbamoyl group; a N-sec-butyl-N-methylcarbamoyl group; a N-tert-butyl-N-methylcarbamoyl group; a N-ethyl-N-propylcarbamoyl group; a N-ethyl-N-isopropylcarbamoyl group; a N-butyl-N-ethylcarbamoyl group; a N-sec-butyl-N-ethylcarbamoyl group; a N-tert-butyl-N-ethylcarbamoyl group; a N-isopropyl-N-propylcarbamoyl group; a N-butyl-N-propylcarbamoyl group; a N-sec-butyl-N-propylcarbamoyl group; a N-tert-butyl-N-propylcarbamoyl group; a N-butyl-N-isopropylcarbamoyl group; a N-sec-butyl-N-isopropylcarbamoyl group; a N-tert-butyl-N-isopropylcarbamoyl group; a N-butyl-N-sec-butylcarbamoyl group; a N-butyl-N-tert-butylcarbamoyl group; a N-sec-butyl-N-tert-butylcarbamoyl group; a methoxy group; an ethoxy group; a propoxy group;

an isopropoxy group; a butoxy group; a sec-butoxy group; a tert-butoxy group; a pentyloxy group; a hexyloxy group; a methoxycarbonyl group; an ethoxycarbonyl group; a propoxycarbonyl group; an isopropoxycarbonyl group; a butoxycarbonyl group; a sec-butoxycarbonyl group; a tert-butoxycarbonyl group; a pentyloxycarbonyl group; a hexyloxycarbonyl group; a formyl group; an acetyl group; a propionyl group; a butyryl group; an isobutyryl group; a valeryl group; an isovaleryl group; a pivaloyl group; an acryloyl group; a propioyl group; a phenyl group; a naphthyl group; a 3-10-membered monocyclic or fused polycyclic nonaromatic heterocyclic group containing one or more than one heteroatom (an oxyranyl group; an aziridinyl group; an oxetanyl group; a thietanyl group; a thioranyl group; a thiomorpholinyl group; a pyrrolidinyl group; a pyrrolinyl group; an imidazolidinyl group; an imidazolinyl group; a tetrahydrofuryl group; a pyrazolidinyl group; a pyrazolinyl group; a pyranyl group; a tetrahydropyranyl group; a piperazinyl group; a morpholinyl group; a piperidinyl group; an indolinyl group; an isoindolinyl group; a dihydrobenzofuranyl group; an oxobenzothiazolinyl group etc.); a 5-10-membered monocyclic or fused polycyclic heteroaryl group containing one or more than one heteroatom (a thiazolyl group; a thienyl group; a furyl group; an isothiazolyl group; an oxazolyl group; an isoxazolyl group; a pyrrolyl group; a imidazolyl group; a furazanyl group; a pyrazolyl group; a pyridyl group; a pyrazinyl group; a pyrimidinyl group; a pyridazinyl group; a triazinyl group; a quinolyl group; an isoquinolyl group; an indolyl group; an isoindolyl group; an indolidinyl group; an indazolyl group; a phthalazinyl group; a naphthilidinyl group; a quinoxalinyl group; a quinazolinyl group; a prinyl group; a pteridinyl group; a synnolinyl group; a chromenyl group; a benzofuranyl group; a benzooxazolyl group; a benzisoxazolyl group; a benzothiazolyl group; a benzisothiazolyl group; a benzimidazolyl group etc.)), a 3-7-membered monocyclic nonaromatic heterocyclic group (an oxyranyl group; an aziridinyl group; an oxetanyl group; a thietanyl group; a thioranyl group; a thiomorpholinyl group; a pyrrolidinyl group; a pyrrolinyl group; an imidazolidinyl group; an imidazolinyl group; a tetrahydrofuryl group; a pyrazolidinyl group; a pyrazolinyl group; a pyranyl group; a tetrahydropyranyl group; a piperazinyl group; a morpholinyl group; a piperidinyl group etc.) or an indanyl group containing one or more than one heteroatom optionally having one or more than one substituent group (fluorine; chlorine; bromine; iodine; a hydroxy group; a nitro group; a cyano group; an amino group; a carboxyl group; a methyl group; an ethyl group; a propyl group; a butyl group; a pentyl group; a hexyl group; an isopropyl group; a sec-butyl group; a tert-butyl group; an isopentyl group; a neopentyl group; a 1-methylpropyl group; an isohexyl group; a 1,1-dimethylbutyl group; a 2,2-dimethylbutyl group; a 3,3-dimethylbutyl group; a $C_3$-$C_7$ cycloalkyl group (a cyclopropyl group; a cyclobutyl group; a cyclopentyl group; a cyclohexyl group; a cycloheptyl group etc.) optionally having a substituent group (a phenyl group; a methyl group; an ethyl group; a propyl group; a butyl group; a pentyl group; a hexyl group; an isopropyl group; a sec-butyl group; a tert-butyl group; an isopentyl group; a neopentyl group; a 1-methylpropyl group; an isohexyl group; a 1,1-dimethylbutyl group; a 2,2-dimethylbutyl group; a 3,3-dimethylbutyl group etc.); a $C_1$-$C_6$ alkyl group (a methyl group; an ethyl group; a propyl group; a butyl group; a pentyl group; a hexyl group; an isopropyl group; a sec-butyl group; a tert-butyl group; an isopentyl group; a neopentyl group; a 1-methylpropyl group; an isohexyl group; a 1,1-dimethylbutyl group; a 2,2-dimethylbutyl group; a 3,3-dimethylbutyl group etc.) having one or more than one halogen atom (fluorine; chlorine; bromine; iodine); a carbamoyl group; a methylcarbamoyl group; an ethylcarbamoyl group; a propylcarbamoyl group; an isopropylcarbamoyl group; a butylcarbamoyl group; a sec-butylcarbamoyl group; a tert-butylcarbamoyl group; a dimethylcarbamoyl group; a diethylcarbamoyl group; a dipropylcarbamoyl group; a diisopropylcarbamoyl group; a dibutylcarbamoyl group; a di-sec-butylcarbamoyl group; a di-tert-butylcarbamoyl group; a N-ethyl-N-methylcarbamoyl group; a N-methyl-N-propylcarbamoyl group; a N-isopropyl-N-methylcarbamoyl group; a N-butyl-N-methylcarbamoyl group; a N-sec-butyl-N-methylcarbamoyl group; a N-tert-butyl-N-methylcarbamoyl group; a N-ethyl-N-propylcarbamoyl group; a N-ethyl-N-isopropylcarbamoyl group; a N-butyl-N-ethylcarbamoyl group; a N-sec-butyl-N-ethylcarbamoyl group; a N-tert-butyl-N-ethylcarbamoyl group; a N-isopropyl-N-propylcarbamoyl group; a N-butyl-N-propylcarbamoyl group; a N-sec-butyl-N-propylcarbamoyl group; a N-tert-butyl-N-propylcarbamoyl group; a N-butyl-N-isopropylcarbamoyl group; a N-sec-butyl-N-isopropylcarbamoyl group; a N-tert-butyl-N-isopropylcarbamoyl group; a N-butyl-N-sec-butylcarbamoyl group; a N-butyl-N-tert-butylcarbamoyl group; a N-sec-butyl-N-tert-butylcarbamoyl group; a methoxy group; an ethoxy group; a propoxy group; an isopropoxy group; a butoxy group; a sec-butoxy group; a tert-butoxy group; a pentyloxy group; a hexyloxy group; a methoxycarbonyl group; an ethoxycarbonyl group; a propoxycarbonyl group; an isopropoxycarbonyl group; a butoxycarbonyl group; a sec-butoxycarbonyl group; a tert-butoxycarbonyl group; a pentyloxycarbonyl group; a hexyloxycarbonyl group; a formyl group; an acetyl group; a propionyl group; a butyryl group; an isobutyryl group; a valeryl group; an isovaleryl group; a pivaloyl group; an acryloyl group; a propioyl group; a phenyl group; a naphthyl group; a 3-10-membered monocyclic or fused polycyclic nonaromatic heterocyclic group containing one or more than one heteroatom (an oxyranyl group; an aziridinyl group; an oxetanyl group; a thietanyl group; a thioranyl group; a thiomorpholinyl group; a pyrrolidinyl group; a pyrrolinyl group; an imidazolidinyl group; an imidazolinyl group; a tetrahydrofuryl group; a pyrazolidinyl group; a pyrazolinyl group; a pyranyl group; a tetrahydropyranyl group; a piperazinyl group; a morpholinyl group; a piperidinyl group; an indolinyl group; an isoindolinyl group; a dihydrobenzofuranyl group; an oxobenzothiazolinyl group etc.); a 5-10-membered monocyclic or fused polycyclic heteroaryl group containing one or more than one heteroatom (a thiazolyl group; a thienyl group; a furyl group; an isothiazolyl group; an oxazolyl group; an isoxazolyl group; a pyrrolyl group; a imidazolyl group; a furazanyl group; a pyrazolyl group; a pyridyl group; a pyrazinyl group; a pyrimidinyl group; a pyridazinyl group; a triazinyl group; a quinolyl group; an isoquinolyl group; an indolyl group; an isoindolyl group; an indolidinyl group; an indazolyl group; a phthalazinyl group; a naphthilidinyl group; a quinoxalinyl group; a quinazolinyl group; a prinyl group; a pteridinyl group; a synnolinyl group; a chromenyl group; a benzofuranyl group; a benzooxazolyl group; a benzisoxazolyl group; a benzothiazolyl group; a benzisothiazolyl group; a benzimidazolyl group etc.)), as $R_3$, there can be mentioned a hydrogen atom, a $C_1$-$C_8$ alkyl group (a methyl group; an ethyl group; a propyl group; a butyl group; a pentyl group; a hexyl group; an isopentyl group; a neopentyl group; a 1-methylpropyl group; an isohexyl group; a 1,1-dimethylbutyl group; a 2,2-dimethylbutyl group; a 3,3-dimethylbutyl group; a heptyl group or an octyl group etc.) optionally having one or more than one substituent group (fluorine; chlorine; bromine; iodine; a hydroxy group; a nitro group; a cyano group; an amino group; a carboxyl group; a methyl group; an ethyl group; a propyl group; a butyl group; a pentyl group; a hexyl group; an isopropyl group; a sec-butyl group; a tert-butyl group; an isopentyl group; a neopentyl group; a 1-methylpropyl group; an isohexyl group; a 1,1-dimethylbutyl group; a 2,2-dimethylbutyl group; a 3,3-dimethylbutyl group; a $C_3$-$C_7$ cycloalkyl group (a cyclopropyl group; a cyclobutyl group; a cyclopentyl group; a cyclohexyl group; a cycloheptyl group etc.) optionally having a substituent group (a phenyl group; a methyl group; an ethyl group; a propyl group; a butyl group; a pentyl group; a hexyl group; an isopropyl group; a sec-butyl group; a tert-butyl group; an isopentyl group; a neopentyl group; a 1-methylpropyl group; an isohexyl group; a 1,1-dimethylbutyl group; a 2,2-dimethylbutyl group; a 3,3-dimethylbutyl group etc.); a $C_1$-$C_6$ alkyl group (a methyl group; an ethyl group; a propyl group; a butyl group; a pentyl group or a hexyl group; an isopropyl group; a sec-butyl group; a tert-butyl group; an isopentyl group; a neopentyl group; a 1-methylpropyl group; an isohexyl group; a 1,1-dimethylbutyl group; a 2,2-dimethylbutyl group; a 3,3-dimethylbutyl group etc.) having one or more than one halogen atom (fluorine; chlorine; bromine; iodine); a carbamoyl group; a methylcarbamoyl group; an ethylcarbamoyl group; a propylcarbamoyl group; an isopropylcarbamoyl group; a butylcarbamoyl group; a sec-butylcarbamoyl group; a tert-butylcarbamoyl group; a dimethylcarbamoyl group; a diethylcarbamoyl group; a dipropylcarbamoyl group; a diisopropylcarbamoyl group; a dibutylcarbamoyl group; a di-sec-butylcarbamoyl group; a di-tert-butylcarbamoyl group; a N-ethyl-N-methylcarbamoyl group; a N-methyl-N-propylcarbamoyl group; a N-isopropyl-N-methylcarbamoyl group; a N-butyl-N-methylcarbamoyl group; a N-sec-butyl-N-methylcarbamoyl group; a N-tert-butyl-N-methylcarbamoyl group; a N-ethyl-N-propylcarbamoyl group; a N-ethyl-N-isopropylcarbamoyl group; a N-butyl-N-ethylcarbamoyl group; a N-sec-butyl-N-ethylcarbamoyl group; a N-tert-butyl-N-ethylcarbamoyl group; a N-isopropyl-N-propylcarbamoyl group; a N-butyl-N-propylcarbamoyl group; a N-sec-butyl-N-propylcarbamoyl group; a N-tert-butyl-N-propylcarbamoyl group; a N-butyl-N-isopropylcarbamoyl group; a N-sec-butyl-N-isopropylcarbamoyl group; a N-tert-butyl-N-isopropylcarbamoyl group; a N-butyl-N-sec-butylcarbamoyl group; a N-butyl-N-tert-butylcarbamoyl group; a N-sec-butyl-N-tert-butylcarbamoyl group; a methoxy group; an ethoxy group; a propoxy group; an isopropoxy group; a butoxy group; a sec-butoxy group; a tert-butoxy group; a pentyloxy group; a hexyloxy group; a methoxycarbonyl group; an ethoxycarbonyl group; a propoxycarbonyl group; an isopropoxycarbonyl group; a butoxycarbonyl group; a sec-butoxycarbonyl group; a tert-butoxycarbonyl group; a pentyloxycarbonyl group; a hexyloxycarbonyl group; a formyl group; an acetyl group; a propionyl group; a butyryl group; an isobutyryl group; a valeryl group; an isovaleryl group; a pivaloyl group; an acryloyl group; a propioyl group; a phenyl group; a naphthyl group; a 3-10-membered monocyclic or fused polycyclic nonaromatic heterocyclic group containing one or more than one heteroatom (an oxyranyl group; an aziridinyl group; an oxetanyl group; a thietanyl group; a thioranyl group; a thiomorpholinyl group; a pyrrolidinyl group; a pyrrolinyl group; an imidazolidinyl group; an imidazolinyl group; a tetrahydrofuryl group; a pyrazolidinyl group; a pyrazolinyl group; a pyranyl group; a tetrahydropyranyl group; a piperazinyl group; a morpholinyl group; a piperidinyl group; an indolinyl group; an isoindolinyl group; a dihydrobenzofuranyl group; an oxobenzothiazolinyl group etc.); a 5-10-membered monocyclic or fused polycyclic heteroaryl group containing one or more than one heteroatom (a thiazolyl group; a thienyl group; a furyl group; an isothiazolyl group; an oxazolyl group; an isoxazolyl group; a pyrrolyl group; a imidazolyl group; a furazanyl group; a pyrazolyl group; a pyridyl group; a pyrazinyl group; a pyrimidinyl group; a pyridazinyl group; a triazinyl group; a quinolyl group; an isoquinolyl group; an indolyl group; an isoindolyl group; an indolidinyl group; an indazolyl group; a phthalazinyl group; a naphthilidinyl group; a quinoxalinyl group; a quinazolinyl group; a prinyl group; a pteridinyl group; a synnolinyl group; a chromenyl group; a benzofuranyl group; a benzooxazolyl group; a benzisoxazolyl group; a benzothiazolyl group; a benzisothiazolyl group; a benzimidazolyl group etc.)), a $C_3$-$C_7$ cycloalkyl group (a cyclopropyl group; a cyclobutyl group; a cyclopentyl group; a cyclohexyl group; a cycloheptyl group), a 3-7-membered monocyclic nonaromatic heterocyclic group containing one or more than one heteroatom (an oxyranyl group; an aziridinyl group; an oxetanyl group; a thietanyl group; a thioranyl group; a thiomorpholinyl group; a pyrrolidinyl group; a pyrrolinyl group; a tetrahydrofuryl group; an imidazolidinyl group; an imidazolinyl group; a pyrazolidinyl group; a pyrazolinyl group; a pyranyl group; a tetrahydropyranyl group; a piperazinyl group; a morpholinyl group; a piperidinyl group etc.), a 6-10-membered monocyclic or fused polycyclic aryl group (a phenyl group; a naphthyl group etc.) or a 5-10-membered monocyclic or fused polycyclic heteroaryl group containing one or more than one heteroatom (a thiazolyl group; a thienyl group; a furyl group; an isothiazolyl group; an oxazolyl group; an isoxazolyl group; a pyrrolyl group; an imidazolyl group; a furazanyl group; a pyrazolyl group; a pyridyl group; a pyrazinyl group; a pyrimidinyl group; a pyridazinyl group; a triazinyl group; a quinolyl group; an isoquinolyl group; an indolyl group; an isoindolyl group; an indolidinyl group; an indazolyl group; a phthalazinyl group; a naphthilidinyl group; a quinoxalinyl group; a quinazolinyl group; a purinyl group; a pteridinyl group; a cinnolinyl group; a chromenyl group; a benzofuranyl group; a benzooxazolyl group; a benzisoxazolyl group; a benzothiazolyl group; a benzisothiazolyl group; a benzimidazolyl group etc.).

As $R_4$, there can be mentioned a hydrogen atom, a methyl group, an ethyl group, a propyl group, an isopropyl group, a butyl group, a sec-butyl group, a tert-butyl group, a pentyl group, a 2-pentyl group, a 3-pentyl group, a neopentyl group, a hexyl group, a 2-hexyl group, a 3-hexyl group, a 2-ethylbutyl group, and the like.

Some of the compounds of the above general formula (I) have an asymmetric carbon atom, and thus may exist as optical isomers, which are also encompassed in the present invention. The salts of compounds of the above general formula (I) and the optical isomers thereof are also encompassed in the present invention. As the salts, pharmaceutically acceptable ones may be preferred including, for example, inorganic acid salts such as hydrochlorides, hydrobromides, hydroiodides and phosphates, and organic acid salts such as oxalates, maleates, fumarates, lactates, malates, citrates, tartrates, benzoates, methansulfonates, p-toluenesulfonates etc.

Furthermore, examples of specific substituent groups of $R_1$-$R_4$ in the compounds of general formula (I) of the present invention are shown hereinbelow, but the present invention is not limited to these examples in any way.

As $R_1$, there can be mentioned, for example, a methyl group, an ethyl group, a propyl group, a butyl group, a pentyl group, a hexyl group, an isopropyl group, a sec-butyl group, a tert-butyl group, an isopentyl group, a neopentyl group, a 1-methylpropyl group, an isohexyl group, a 1,1-dimethylbutyl group, a 2,2-dimethylbutyl group, a 3,3-dimethylbutyl group, a 2-ethylbutyl group, a benzyl group, a phenetyl group, a 2-furylmethyl group, a 3-furylmethyl group, a 2-(2-furyl)ethyl group, a 2-(3-furyl)ethyl group, a 3-(2-furyl)propyl group, a 3-(3-furyl)propyl group, a 4-(2-furyl)furylbutyl group, a 4-(3-furyl)furylbutyl group, a 5-(2-furyl)furylpentyl group, a 5-(3-furyl)furylpentyl group, a cyclopropyl group, a cyclobutyl group, a cyclopentyl group, a cyclohexyl group, an oxyranyl group, an oxetanyl group, a thietanyl group, a thioranyl group, a thiomorpholinyl group, a pyrrolidinyl group, a pyrrolinyl group, a tetrahydrofuryl group, an indanyl group, a fluoromethyl group, a 2-fluoroethyl group, a 3-fluoropropyl group, a fluorocyclopropyl group, a fluorocyclopentyl group, a fluorotetrahydrofuryl group, a hydroxymethyl group, a 2-hydroxyethyl group, a 3-hydroxypropyl group, a 1-hydroxycyclopropyl group, a hydroxycyclopentyl group, a hydroxytetrahydrofuryl group, a nitromethyl group, a 2-nitroethyl group, a 3-nitropropyl group, a nitrocyclopropyl group, a nitrocyclopentyl group, a nitrotetrahydrofuryl group, a cyanomethyl group, a 2-cyanoethyl group, a 3-cyanopropyl group, a cyanocyclopropyl group, a cyanocyclopentyl group, a cyanotetrahydrofuryl group, an acetylmethyl group, a 2-acetylethyl group, a 3-acetylpropyl group, an acetylcyclopropyl group, an acetylcyclopentyl group, a 1-methylcyclopropyl group, a methylcyclopentyl group, a methyltetrahydrofuryl group, a 1-ethylcyclopropyl group, an ethylcyclopentyl group, an ethyltetrahydrofuryl group, a cyclopropylmethyl group, a (1-phenylcyclopropyl)methyl group, a phenylcyclopropylethyl group, a phenylcyclopropylpropyl group, a phenylcyclopropylcyclopropyl group, a phenylcyclopropylcyclopentyl group, a phenylcyclopropyltetrahydrofuryl group, a phenylcyclopentylmethyl group, a phenylcyclopentylethyl group, a phenylcyclopentylpropyl group, a (1-methylcyclopropyl)methyl group, a 2-(1-methylcyclopropyl)ethyl group, a 3-(1-methylcyclopropyl)propyl group, a methylcyclopropyltetrahydrofuryl group, a methylcyclopentylmethyl group, a methylcyclopentylethyl group, a methylcyclopentylpropyl group, a methylcyclopentylcyclopropyl group, a methylcyclopentylcyclopentyl group, a methylcyclopentyltetrahydrofuryl group, a fluoromethylcyclopropyl group, a fluoromethylcyclopentyl group, a fluoromethyltetrahydrofuryl group, a carbamoylmethyl group, a carbamoylethyl group, a carbamoylpropyl group, a methylcarbamoylmethyl group, an ethylcarbamoylmethyl group, a propylcarbamoylmethyl group, an isopropylcarbamoylmethyl group, a butylcarbamoylmethyl group, a sec-butylcarbamoylmethyl group, a tert-butylcarbamoylmethyl group, a dimethylcarbamoylmethyl group, a diethylcarbamoylmethyl group, a dipropylcarbamoylmethyl group, a diisopropylcarbamoylmethyl group, a dibutylcarbamoylmethyl group, a di-sec-butylcarbamoylmethyl group, a di-tert-butylcarbamoylmethyl group, a N-ethyl-N-methylcarbamoylmethyl group, a N-methyl-N-propylcarbamoylmethyl group, a N-isopropyl-N-methylcarbamoylmethyl group, a N-butyl-N-methylcarbamoylmethyl group, a N-sec-butyl-N-methylcarbamoylmethyl group, a N-tert-butyl-N-methylcarbamoylmethyl group, a N-ethyl-N-propylcarbamoylmethyl group, a N-ethyl-N-isopropylcarbamoylmethyl group, a N-butyl-N-ethylcarbamoylmethyl group, a N-sec-butyl-N-ethylcarbamoylmethyl group, a N-tert-butyl-N-ethylcarbamoylmethyl group, a N-isopropyl-N-propylcarbamoylmethyl group, a N-butyl-N-propylcarbamoylmethyl group, a N-sec-butyl-N-tert-butylcarbamoylmethyl group, a N-sec-butyl-N-propylcarbamoylmethyl group, a N-tert-butyl-N-propylcarbamoylmethyl group, a N-butyl-N-isopropylcarbamoylmethyl group, a N-sec-butyl-N-isopropylcarbamoylmethyl group, a N-tert-butyl-N-isopropylcarbamoylmethyl group, a N-butyl-N-sec-butylcarbamoylmethyl group, a N-butyl-N-tert-butylcarbamoylmethyl group, a methylcarbamoylethyl group, a dimethylcarbamoylethyl group, a diethylcarbamoylethyl group, an ethylcarbamoylethyl group, a methylcarbamoylpropyl group, an ethylcarbamoylpropyl group, a dimethylcarbamoylpropyl group, a diethylcarbamoylpropyl group, a methylcarbamoylbutyl group, an ethylcarbamoylbutyl group, a dimethylcarbamoylbutyl group, a diethylcarbamoylbutyl group, an ethylcarbamoylpentyl group, a propylcarbamoylpentyl group, a dimethylcarbamoylpentyl group, a diethylcarbamoylpentyl group, a carbamoylcyclopropyl group, a carbamoylcyclopentyl group, a carbamoyltetrahydrofuryl group, a methoxymethyl group, a methoxyethyl group, a methoxypropyl group, a methoxycyclopropyl group, a methoxycyclopentyl group, a methoxytetrahydrofuryl group, an ethoxymethyl group, an ethoxyethyl group, an ethoxypropyl group, an ethoxycyclopropyl group, an ethoxycyclopentyl group, an ethoxytetrahydrofuryl group, a methoxycarbonylmethyl group, a methoxycarbonylethyl group, a methoxycarbonylpropyl group, a methoxycarbonylcyclopropyl group, a methoxycarbonylcyclopentyl group, a methoxycarbonyltetrahydrofuryl group, a 2-pyridylmethyl group, a 3-pyridylmethyl group, a 4-pyridylmethyl group, a 2-(2-pyridyl)ethyl group, a 2-(3-pyridyl)ethyl group, a 2-(4-pyridyl)ethyl group, a 3-(2-pyridyl)propyl group, a 3-(3-pyridyl)propyl group, a 3-(4-pyridyl)propyl group, a pyridylcyclopropyl group, a pyridylcyclopentyl group, a pyridyltetrahydrofuryl group, a 3-phenylpropyl group, a phenylcyclopropyl group, a phenylcyclopentyl group, a phenyltetrahydrofuryl group, a 2-thiazolylmethyl group, a 2-(2-thiazolyl)ethyl group, a 3-(2-thiazolyl)thiazolylpropyl group, a thiazolylcyclopropyl group, a thiazolylcyclopentyl group, a furylcyclopropyl group, a 2-thienylmethyl group, a 3-thienylmethyl group, a 2-(2-thienyl)ethyl group, a 2-(3-thienyl)ethyl group, a 3-(2-thienyl)propyl group, a 3-(3-thienyl)propyl group, a thienylcyclopropyl group, a thienylcyclopentyl group, a 1-naphthylmethyl group, a 2-naphthylmethyl group, a 2-(1-naphthyl)ethyl group, a 2-(2-naphthyl)ethyl group, a 3-(1-naphthyl)propyl group, a 3-(2-naphthyl)propyl group, a naphthylcyclopropyl group, and a naphthylcyclopentyl group.

As $R_2$, there can be mentioned, for example, a methyl group, an ethyl group, a propyl group, an isopropyl group, a butyl group, a sec-butyl group, a tert-butyl group, a difluoromethyl group, a trifluoromethyl group, a fluoromethyl group, a chloromethyl group, a dichloromethyl group, a trichloromethyl group, a bromomethyl group, an iodomethyl group etc., and preferably a methyl group, an ethyl group, a difluoromethyl group, or a trifluoromethyl group may be mentioned.

As $R_3$, there can be mentioned, for example, a hydrogen atom, a methyl group, an ethyl group, a butyl group, a phenyl group, a benzyl group, a phenetyl group, a 2-pyridylmethyl group, a 3-pyridylmethyl group, a 4-pyridylmethyl group, a 2-(2-pyridyl)ethyl group, a 2-(3-pyridyl)ethyl group, a 2-(4-pyridyl)ethyl group, a fluoromethyl group, a 1-fluoroethyl group, a 2-fluoroethyl group, a 1-fluoropropyl group, a 2-fluoropropyl group, a 3-fluoropropyl group, a difluoromethyl group, a trifluoromethyl group, a hydroxymethyl group, a 2-hydroxyethyl group, a 3-hydroxypropyl group, a nitromethyl group, a 2-nitroethyl group, a 2-nitropropyl group, a 3-nitropropyl group, a cyanomethyl group, a 2-cyanoethyl group, a 3-cyanopropyl group, an acetylmethyl group, a 2-acetylethyl group, a 3-acetylpropyl group, a (1-phenylcyclopropyl)methyl group, a 2-(1-phenylcyclopropyl)ethyl group, a 3-(1-phenylcyclopropyl)propyl group, a (1-phenylcyclopentyl)methyl group, a 2-(1-phenylcyclopentyl)ethyl group, a 3-(1-phenylcyclopentyl)propyl group, a (1-methylcyclopropyl)methyl group, a 2-(1-methylcyclopropyl)ethyl group, a 3-(1-methylcyclopropyl)propyl group, a methylcyclopentylmethyl group, a methylcyclopentylethyl group, a methylcyclopentylpropyl group, a carbamoylmethyl group, a carbamoylethyl group, a carbamoylpropyl group, a methylcarbamoylmethyl group, an ethylcarbamoylmethyl group, a propylcarbamoylmethyl group, an isopropylcarbamoylmethyl group, a butylcarbamoylmethyl group, a sec-butylcarbamoylmethyl group, a tert-butylcarbamoylmethyl group, a dimethylcarbamoylmethyl group, a diethylcarbamoylmethyl group, a dipropylcarbamoylmethyl group, a diisopropylcarbamoylmethyl group, a dibutylcarbamoylmethyl group, a di-sec-butylcarbamoylmethyl group, a di-tert-butylcarbamoylmethyl group, a N-ethyl-N-methylcarbamoylmethyl group, a N-methyl-N-propylcarbamoylmethyl group, a N-isopropyl-N-methylcarbamoylmethyl group, a N-butyl-N-methylcarbamoylmethyl group, a N-sec-butyl-N-methylcarbamoylmethyl group, a N-tert-butyl-N-methylcarbamoylmethyl group, a N-ethyl-N-propylcarbamoylmethyl group, a N-ethyl-N-isopropylcarbamoylmethyl group, a N-butyl-N-ethylcarbamoylmethyl group, a N-sec-butyl-N-ethylcarbamoylmethyl group, a N-tert-butyl-N-ethylcarbamoylmethyl group, a N-isopropyl-N-propylcarbamoylmethyl group, a N-butyl-N-propylcarbamoylmethyl group, a N-sec-butyl-N-tert-butylcarbamoylmethyl group, a N-sec-butyl-N-propylcarbamoylmethyl group, a N-tert-butyl-N-propylcarbamoylmethyl group, a N-butyl-N-isopropylcarbamoylmethyl group, a N-sec-butyl-N-isopropylcarbamoylmethyl group, a N-tert-butyl-N-isopropylcarbamoylmethyl group, a N-butyl-N-sec-butylcarbamoylmethyl group, a N-butyl-N-tert-butylcarbamoylmethyl group, a methylcarbamoylethyl group, a dimethylcarbamoylethyl group, a diethylcarbamoylethyl group, an ethylcarbamoylethyl group, a methylcarbamoylpropyl group, an ethylcarbamoylpropyl group, a dimethylcarbamoylpropyl group, a diethylcarbamoylpropyl group, a methylcarbamoylbutyl group, an ethylcarbamoylbutyl group, a dimethylcarbamoylbutyl group, a diethylcarbamoylbutyl group, an ethylcarbamoylpentyl group, a propylcarbamoylpentyl group, a dimethylcarbamoylpentyl group, a diethylcarbamoylpentyl group, a methoxymethyl group, a methoxyethyl group, a methoxypropyl group, an ethoxymethyl group, an ethoxyethyl group, an ethoxypropyl group, a methoxycarbonylmethyl group, a methoxycarbonylethyl group, a methoxycarbonylpropyl group, a 3-(2-pyridyl)propyl group, a 3-(3-pyridyl)propyl group, a 3-(4-pyridyl)propyl group, a 3-phenylpropyl group, a 2-thiazolylmethyl group, a 2-(2-thiazolyl)ethyl group, a 3-(2-thiazolyl)propyl group, a 2-furylmethyl group, a 3-furylmethyl group, a 2-(2-furyl)ethyl group, a 2-(3-furyl)ethyl group, a 3-(2-furyl)propyl group, a 3-(3-furyl)propyl group, a 2-thienylmethyl group, a 3-thienylmethyl group, a 2-(2-thienyl)ethyl group, a 2-(3-thienyl)ethyl group, a 3-(2-thienyl)propyl group, a 3-(3-thienyl)propyl group, a 1-naphthylmethyl group, a 2-naphthylmethyl group, a 2-(1-naphthyl)ethyl group, a 2-(2-naphthyl)ethyl group, a 3-(1-naphthyl)propyl group, a 3-(2-naphthyl)propyl group, 2-oxybenzothiazolinyl-3-ylmethyl group, a cyclopropyl group, a cyclopentyl group, a tetrahydrofuryl group, a 2-pyridyl group, a 3-pyridyl group, a 4-pyridyl group, a 2-furyl group, and a 3-furyl group.

As $R_4$, there can be mentioned, for example, a hydrogen atom, a methyl group, an ethyl group, a propyl group, an isopropyl group, a butyl group, a sec-butyl group, a tert-butyl group, a 1-methylpropyl group, a pentyl group, an isopentyl group, a neopentyl group, a hexyl group, an isohexyl group, a 1-ethylbutyl group, a 2-ethylbutyl group, a 3-ethylbutyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, etc.

As used herein a $C_1$-$C_8$ alkyl group is a linear group only composed of 1-8 carbons, and there can be mentioned, for example, a methyl group, an ethyl group, a propyl group, a butyl group, an isopropyl group, a sec-butyl group, a tert-butyl group, a pentyl group, an isopentyl group, a 3-pentyl group, a neopentyl group, a 1-methylpropyl group, a hexyl group, an isohexyl group, a heptyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1-ethylbutyl group, a 2-ethylbutyl group, a 3-ethylbutyl group, a 1,1-diethylbutyl group, a 1,2-diethylbutyl group, a 2,2-diethylbutyl group, a 1,1,2-trimethylbutyl group, a 1,1,3-trimethylbutyl group, a 1,2,2-trimethylbutyl group, a 1,2,3-trimethylbutyl group, a 1,3,3-trimethylbutyl group, a 2,2,3-trimethylbutyl group, a 2,3,3-trimethylbutyl group, a 1-methylpentyl group, a 2-methylpentyl group, a 3-methylpentyl group, a 4-methylpentyl group, a 1,1-dimethylpentyl group, a 1,2-dimethylpentyl group, a 1,3-dimethylpentyl group, a 1,4-dimethylpentyl group, a 2,2-dimethylpentyl group, a 2,3-dimethylpentyl group, a 2,4-dimethylpentyl group, a 3,3-dimethylpentyl group, a 3,4-dimethylpentyl group, a 4,4-dimethylpentyl group, a 1,1,2-trimethylpentyl group, a 1,1,3-trimethylpentyl group, a 1,1,4-trimethylpentyl group, a 1,2,2-trimethylpentyl group, a 1,2,3-trimethylpentyl group, a 1,2,4-trimethylpentyl group, a 1,3,3-trimethylpentyl group, a 1,3,4-trimethylpentyl group, a 1,4,4-trimethylpentyl group, a 2,2,3-trimethylpentyl group, a 2,2,4-trimethylpentyl group, a 2,3,4-trimethylpentyl group, a 2,4,4-trimethylpentyl group, a 3,3,4-trimethylpentyl group, a 3,4,4-trimethylpentyl group, a 1-ethylpentyl group, a 2-ethylpentyl group, a 3-ethylpentyl group, a 4-ethylpentyl group or an octyl group etc.

As used herein a $C_1$-$C_6$ alkyl group is a linear group only composed of 1-6 carbons, and there can be mentioned, for example, a methyl group, an ethyl group, a propyl group, a butyl group, an isopropyl group, a sec-butyl group, a tert-butyl group, a pentyl group, a hexyl group, an isopentyl group, a 3-pentyl group, a neopentyl group, a 1-methylpropyl group, a 1-methylpentyl group, a 2-methylpentyl group, a 3-methylpentyl group, an isohexyl group, a 1-ethylbutyl group, a 2-ethylbutyl group, a 3-ethylbutyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1-diethylbutyl group, a 1,2-diethylbutyl group, a 2,2-diethylbutyl group etc.

As used herein a $C_1$-$C_5$ alkyl group is a linear group only composed of 1-5 carbons, and there can be mentioned, for example, a methyl group, an ethyl group, a propyl group, a butyl group, an isopropyl group, a sec-butyl group, a tert-butyl group, an isopentyl group, a 3-pentyl group, a neopentyl group, a 1-methylbutyl group, a 2-methylbutyl group, a 3-methylbutyl group or a pentyl group etc.

As used herein a $C_1$-$C_4$ alkyl group is a linear group only composed of 1-4 carbons, and there can be mentioned, for example, a methyl group, an ethyl group, a propyl group, a butyl group, an isopropyl group, a sec-butyl group, a tert-butyl group etc.

As used herein a $C_1$-$C_3$ alkyl group is a linear group only composed of 1-3 carbons, and there can be mentioned, for example, a methyl group, an ethyl group, a propyl group, an isopropyl group etc.

As used herein a $C_1$-$C_2$ alkyl group is a linear group only composed of 1-2 carbons, and denotes a methyl group and an ethyl group.

As used herein a $C_3$-$C_7$ cycloalkyl group is a cyclic group only composed of 3-7 carbons, and denotes a cyclopropyl group, a cyclobutyl group, a cyclopentyl group, a cyclohexyl group, a cycloheptyl group etc.

As used herein a $C_4$-$C_6$ cycloalkyl group is a cyclic group only composed of 4-6 carbons, and denotes a cyclobutyl group, a cyclopentyl group, and a cyclohexyl group.

As used herein a halogen atom denotes a fluorine, a chlorine, a bromine, and an iodine.

As used herein a $C_1$-$C_6$ haloalkyl group denotes a $C_1$-$C_6$ alkyl group having one or more than one halogen atom selected from a fluorine, a chlorine, a bromine and an iodine, and there can be mentioned, a for example, a fluoromethyl group, a chloromethyl group, a bromomethyl group, an iodomethyl group, a difluoromethyl group, a dichloromethyl group, a dibromomethyl group, a diiodomethyl group, a trifluoromethyl group, a trichloromethyl group, a tribromomethyl group, a triiodomethyl group, a fluoroethyl group, a chloroethyl group, a bromoethyl group, an iodoethyl group, a fluoropropyl group, a chloropropyl group, a bromopropyl group, an iodopropyl group, a fluorobutyl group, a chlorobutyl group, a bromobutyl group, an iodobutyl group, a fluoropentyl group, a chloropentyl group, a bromopentyl group, an iodopentyl group, a fluorohexyl group, a chlorohexyl group, a bromohexyl group, an iodohexyl group etc.

As used herein a $C_1$-$C_4$ haloalkyl group denotes a $C_1$-$C_4$ alkyl group having one or more than one halogen atom selected from a fluorine, a chlorine, a bromine, an iodine, and there can be mentioned, a for example, a fluoromethyl group, a chloromethyl group, a bromomethyl group, an iodomethyl group, a difluoromethyl group, a dichloromethyl group, a dibromomethyl group, a diiodomethyl group, a trifluoromethyl group, a trichloromethyl group, a tribromomethyl group, a triiodomethyl group, a fluoroethyl group, a chloroethyl group, a bromoethyl group, an iodoethyl group, a fluoropropyl group, a chloropropyl group, a bromopropyl group, an iodopropyl group, a fluorobutyl group, a chlorobutyl group, a bromobutyl group, an iodobutyl group etc.

As used herein an alkoxy group denotes an atomic group represented by R—O (R represents an alkyl group), and a $C_1$-$C_6$ alkoxy is an alkoxy group having 1-6 carbons, and there can be mentioned, for example, a methoxy group, an ethoxy group, a propoxy group, an isopropoxy group, a butoxy group, a sec-butoxy group, a tert-butoxy group, a pentyloxy group, a hexyloxy group etc.

As used herein an acyl group denotes an atomic group of the form (R—CO—) in which a hydroxyl group (OH) has been removed from a carboxylic acid (R—CO—OH: R represents an alkyl group), and an acyl group means an acyl group having 1-6 carbons, and there can be mentioned, for example, a formyl group; an acetyl group; a propionyl group; a butyryl group; an isobutyryl group; a valeryl group; an isovaleryl group; a pivaloyl group; an acryloyl group; and a propioyl group.

As used herein an alkoxycarbonyl group denotes an atomic group represented by R—O—CO— (R represents an alkyl group), and a $C_1$-$C_6$ alkoxycarbonyl group is an alkoxycarbonyl group having 1-6 carbons at the alkyl group site, and there can be mentioned, for example, a methoxycarbonyl group, an ethoxycarbonyl group, a propoxycarbonyl group, an isopropoxycarbonyl group, a butoxycarbonyl group, a sec-butoxycarbonyl group, a tert-butoxycarbonyl group, a pentyloxycarbonyl group, a hexyloxycarbonyl group etc.

As used herein a heteroatom means an atom other than hydrogen or carbon, and for example an oxygen atom, a nitrogen atom and a sulfur atom may be mentioned.

As used herein a carbamoyl group optionally having as a substituent an alkyl group at the nitrogen atom denotes an atomic group represented by (R)(R')—N—CO— (R and R' independently of each other represent a hydrogen atom; an alkyl group), and a carbamoyl group optionally having as a substituent a $C_1$-$C_4$ alkyl group denotes a carbamoyl group optionally having 1-4 carbons at the alkyl group site, and there can be mentioned, for example, a carbamoyl group, a methylcarbamoyl group, an ethylcarbamoyl group, a propylcarbamoyl group, an isopropylcarbamoyl group, a butylcarbamoyl group, a sec-butylcarbamoyl group, a tert-butylcarbamoyl group, a dimethylcarbamoyl group, a diethylcarbamoyl group, a dipropylcarbamoyl group, a diisopropylcarbamoyl group, a dibutylcarbamoyl group, a di-sec-butylcarbamoyl group, a di-tert-butylcarbamoyl group, a N-ethyl-N-methylcarbamoyl group, a N-methyl-N-propylcarbamoyl group, a N-isopropyl-N-methylcarbamoyl group, a N-butyl-N-methylcarbamoyl group, a N-sec-butyl-N-methylcarbamoyl group, a N-tert-butyl-N-methylcarbamoyl group, a N-ethyl-N-propylcarbamoyl group, a N-ethyl-N-isopropylcarbamoyl group, a N-butyl-N-ethylcarbamoyl group, a N-sec-butyl-N-ethylcarbamoyl group, a N-tert-butyl-N-ethylcarbamoyl group, a N-isopropyl-N-propylcarbamoyl group, a N-butyl-N-propylcarbamoyl group, a N-sec-butyl-N-propylcarbamoyl group, a N-tert-butyl-N-propylcarbamoyl group, a N-butyl-N-isopropylcarbamoyl group, a N-sec-butyl-N-isopropylcarbamoyl group, a N-tert-butyl-N-isopropylcarbamoyl group, a N-butyl-N-sec-butylcarbamoyl group, a N-butyl-N-tert-butylcarbamoyl group, a N-sec-butyl-N-tert-butylcarbamoyl group etc.

As used herein a 6-10-membered monocyclic or fused polycyclic aryl group denotes a cyclic group having aromatic properties only composed of 6-10 carbon atoms, and denotes a phenyl group, a naphthyl group etc.

As used herein a 5-10-membered monocyclic or fused polycyclic heteroaryl group denotes an aromatic heterocyclic group composed of 5-10 atoms containing one or more than one heteroatom selected from heteroatoms such as an oxygen atom, a nitrogen atom and a sulfur atom, and there can be mentioned, for example, a thiazolyl group, a thienyl group, a furyl group, an isothiazolyl group, an oxazolyl group, an isoxazolyl group, a pyrrolyl group, an imidazolyl group, a furazanyl group, a pyrazolyl group, a pyridyl group, a pyrazinyl group, a pyrimidinyl group, a pyridazinyl group, a triazinyl group, a quinolyl group, an isoquinolyl group, an indolyl group, an isoindolyl group, an indolidinyl group, an indazolyl group, a phthalazinyl group, a naphthilidinyl group, a quinoxalinyl group, a quinazolinyl group, a prinyl group, a pteridinyl group, a synnolinyl group, a chromenyl group, a benzofuranyl group, a benzooxazolyl group, a benzisoxazolyl group, a benzothiazolyl group, a benzisothiazolyl group, a benzimidazolyl group etc.

As used herein a 5-6-membered monocyclic heteroaryl group denotes a monocyclic aromatic heterocyclic group composed of 5-6 atoms containing one or more than one heteroatom selected from heteroatoms such as an oxygen atom, a nitrogen atom and a sulfur atom, and there can be mentioned, for example, a thiazolyl group, a thienyl group, a furyl group, an isothiazolyl group, an oxazolyl group, an isoxazolyl group, a pyrrolyl group, an imidazolyl group, a furazanyl group, a pyrazolyl group, a pyridyl group, a pyrazinyl group, a pyrimidinyl group, a pyridazinyl group, a triazinyl group etc.

As used herein a 3-10-membered monocyclic or fused polycyclic nonaromatic heterocyclic group containing one or more than one heteroatom denotes a monocyclic or fused polycyclic nonaromatic cyclic group composed of 3-10 atoms containing one or more than one heteroatom selected from heteroatoms such as an oxygen atom, a nitrogen atom and a sulfur atom, and there can be mentioned, for example, an oxyranyl group, an aziridinyl group, an oxetanyl group, a thietanyl group, a thioranyl group, a thiomorpholinyl group, a tetrahydrofuryl group, a pyrrolidinyl group, a pyrrolinyl group, an imidazolidinyl group, an imidazolinyl group, a pyrazolidinyl group, a pyrazolinyl group, a pyranyl group, a tetrahydropyranyl group, a piperazinyl group, a morpholinyl group, a piperidinyl group, an indolinyl group, an isoindolinyl group, a dihydrobenzofuranyl group, a tetrahydroquinolyl group, a tetrahydroisoquinolyl group, an oxobenzothiazolyl group etc.

As used herein a 3-7-membered monocyclic nonaromatic heterocyclic group containing one or more than one heteroatom denotes a monocyclic or fused polycyclic nonaromatic cyclic group composed of 3-7 atoms containing one or more than one heteroatom selected from heteroatoms such as an oxygen atom, a nitrogen atom and a sulfur atom, and there can be mentioned, for example, an oxyranyl group, an aziridinyl group, an oxetanyl group, a thietanyl group, a thioranyl group, a thiomorpholinyl group, a tetrahydrofuryl group, a pyrrolidinyl group, a pyrrolinyl group, an imidazolidinyl group, an imidazolinyl group, a pyrazolidinyl group, a pyrazolinyl group, a pyranyl group, a tetrahydropyranyl group, a piperazinyl group, a morpholinyl group, a piperidinyl group etc.

As used herein a heterocyclic group denotes a monocyclic or fused polycyclic heteroaryl group containing one or more than one heteroatom and a monocyclic or fused polycyclic nonaromatic heterocyclic group containing one or more than one heteroatom, and there can be mentioned, for example, an oxyranyl group, a aziridinyl group, an oxetanyl group, a thietanyl group, a thioranyl group, a thiomorpholinyl group, a tetrahydrofuryl group, a pyrrolidinyl group, a pyrrolinyl group, an imidazolidinyl group, an imidazolinyl group, a pyrazolidinyl group, a pyrazolinyl group, a pyranyl group, a tetrahydropyranyl group, a piperazinyl group, a morpholinyl group, a piperidinyl group, an indolinyl group, an isoindolinyl group, a dihydrobenzofuranyl group, a thiazolyl group, a thienyl group, a furyl group, an isothiazolyl group, an oxazolyl group, an isoxazolyl group, a pyrrolyl group, an imidazolyl group, a furazanyl group, a pyrazolyl group, a pyridyl group, a pyrazinyl group, a pyrimidinyl group, a pyridazinyl group, a triazinyl group, a quinolyl group, an isoquinolyl group, an indolyl group, an isoindolyl group, an indolidinyl group, an indazolyl group, a phthalazinyl group, a naphthilidinyl group, a quinoxalinyl group, a quinazolinyl group, a prinyl group, a pteridinyl group, a synnolinyl group, a chromenyl group, a benzofuranyl group, a benzooxazolyl group, a benzisoxazolyl group, a benzothiazolyl group, a benzisothiazolyl group, a benzimidazolyl group, a tetrahydroquinolyl group, a tetrahydroisoquinolyl group, oxobenzothiazolyl group etc.

Some of the compounds of the above general formula (I) have an asymmetric carbon atom, and thus may exist as optical isomers. These optical isomers are also encompassed in the present invention. The salts of compounds of the above general formula (I) and the optical isomers thereof are also encompassed in the present invention. As the salts, pharmaceutically acceptable ones may be preferred including, for example, inorganic acid salts such as hydrochlorides, hydrobromides, hydroiodides and phasphates, and organic acid salts such as oxalates, maleates, fumarates, lactates, malates, citrates, tartrates, benzoates, methansulfonates, p-toluenesulfonates etc.

Furthermore, the present invention encompasses the compounds of the above general formula (I) and optical isomers thereof and hydrates and solvates thereof. As a solvent for the solvates, there can be mentioned methanol, ethanol, isopropanol, butanol, acetone, ethyl acetate, chloroform etc.

The compounds of the above general formula (I) may be prepared in a known method (Kokai (Japanese Unexamined Patent Publication) No. 50-37800, Kokai No. 60-89421, Kokai No. 4-234369), and examples of the preparation methods are described according to the following reaction scheme.

Preparation Method 1

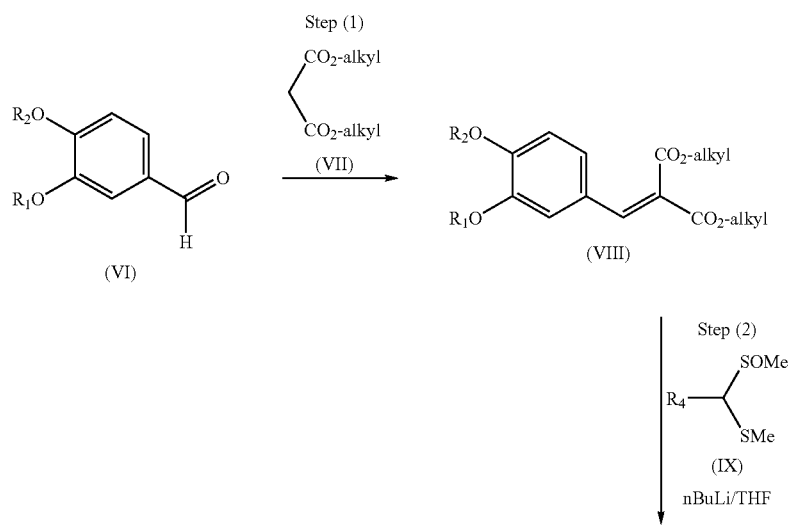

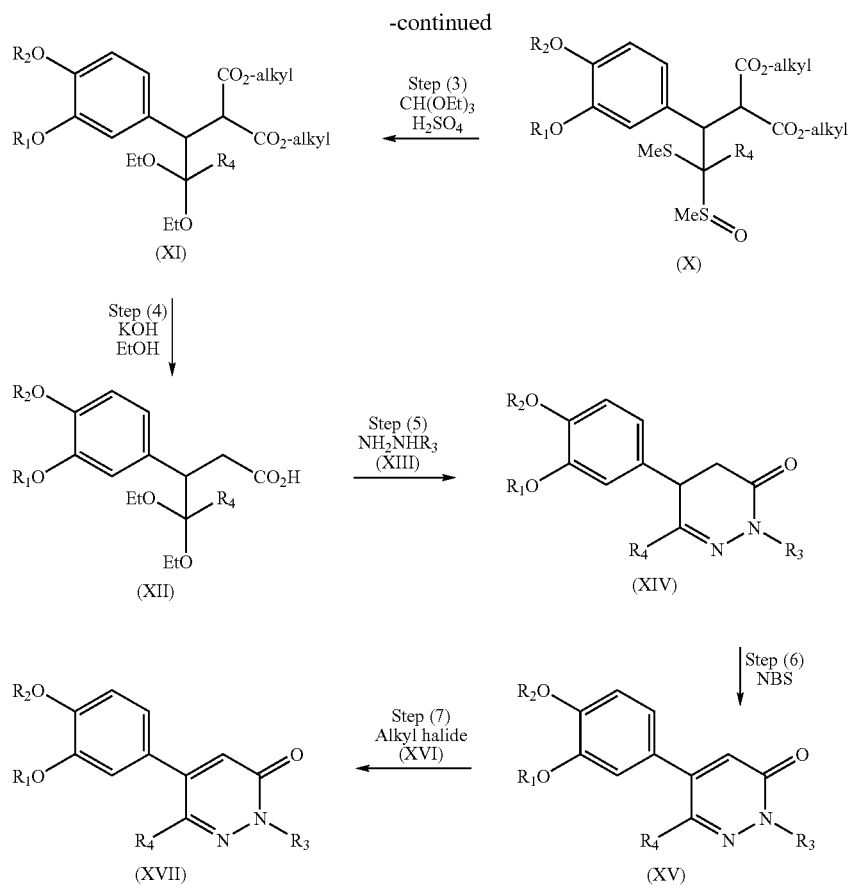

Both of the compounds (XV) and (XVII) in the above reaction scheme correspond to the compounds of the above general formula (I).

Step (1): First, α,β-unsaturated dialkylester (VIII) is synthesized from an aldehyde derivative (VI) and a malonic acid dialkylester derivative (VII) by the Knoevenagel reaction. Generally the reaction may be performed in the presence of a base such as an amine (pyridine etc.), an organic acid salt of an amine, or ammonium acetate in the absence of a solvent or in the presence of an aromatic hydrocarbon solvent such as benzene and toluene that does not inhibit the reaction. The product obtained by this reaction may be isolated by a known method, and used in the subsequent step without further purification.

Step (2): To the α,β-unsaturated dialkylester (VIII), methyl methylsulfinyl-methylsulfide (IX) is reacted in the presence of a base such as n-butyl lithium to synthesize a thioether (X) [J. L. Hermann, et al., Tetrahedron Letters 47, 4707 (1973)]. Generally as a reaction solvent, an ethereal solvent such as diethylether and tetrahydrofuran may be used and the reaction may be performed at a temperature of 0° C. or less. The methyl methylsulfinyl-methylsulfide (IX) as used herein may be prepared in a known method [Ogura, et al., Tetrahedron Letters, 659 (1974)].

Step (3): A thioether (X) in ethanol is reacted with triethyl orthoformate in the presence of a catalytic amount of an acid such as sulfuric acid to synthesize a diethyl acetal (XI). The product obtained in this reaction can be isolated in a known method.

Step (4): The diethyl acetal (XI) is hydrolyzed with a base, followed by decarboxylation and further by acid treatment to be converted to 3-phenyl butyric acid (XII). The base as used herein may be potassium hydroxide, sodium hydroxide etc., and as the solvent, water or an alcohol (ethanol, methanol etc.) may be mentioned.

Step (5): 3-phenyl butyric acid (XII) and a hydrazine (XIII) are reacted to synthesize 2,3,4,5-tetrahydropyridazin-3-one (XIV). The reaction may be performed in the absence or presence of a solvent. As the solvent, any solvent that does not inhibit the reaction may be used including, for example benzene, toluene, xylene, methanol, ethanol, isopropanol, butanol, decaline, tetralin, acetic acid, and water. The reaction temperature may usually be about 0-120° C. The compound obtained in this reaction may be purified in a known method such as crystallization, recrystallization, and chromatography.

Step (6): 2,3,4,5-tetrahydropyridazin-3-one (XIV) is converted to pyridazin-3(2H)-one (XV) in an oxidation reaction. As a combination of reacting reagents as used herein, bromine in acetic acid or N-bromosuccinimide in dimethylsulfoxide may be mentioned. The compound obtained in this reaction may be purified in a known method.

Step (7): When $R_3$ in pyridazin-3(2H)-one (XV) is a hydrogen atom, an alkyl halide (XVI) may be reacted in the presence of a base to synthesize a compound (XVII). X in the formula of the compound (XVI) represents a halogen atom (a chlorine atom, a bromine atom, an iodine atom etc.). As a base for use in this reaction, for example, sodium hydroxide, potassium hydroxide, sodium hydride, potassium carbonate etc. may be mentioned. The reaction may be performed in the absence or presence of a solvent. As the solvent, any solvent that does not inhibit the reaction may be used including, for example, benzene, toluene, xylene, tetrahydrofuran, diethylether, dimethylformamide, dimethylsulfoxide, dichloromethane, and chloroform. The compound obtained in this reaction may be purified in a known method.

Preparation Method 2

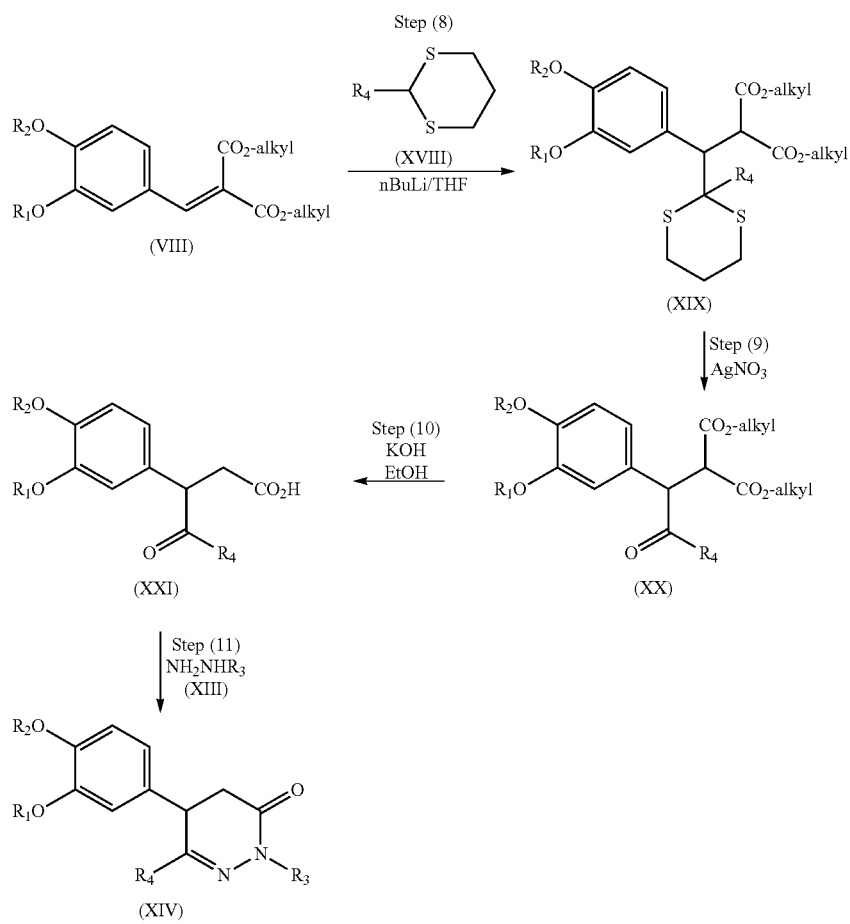

Compound (XIV) which is an intermediate in the synthesis of Compound (I) may also be synthesized in the above method.

Step (8): To the α,β-unsaturated dialkylester (VIII), a 1,3-dithiane (XVIII) may be reacted in the presence of a base such as n-butyl lithium to synthesize a 1,3-dithiane adduct (XIX).

Step (9): 1,3-dithiane adduct (XIX) is deprotected in a known method to synthesize a 4-keto butyric acid ester (XX).

Step (10): 4-keto butyric acid ester (XX) is converted to a 4-keto butyric acid (XXI) in a method similar to step (4).

Step (11): In a method similar to step (5), the 4-keto butyric acid (XXI) and a hydrazine (XIII) are reacted to synthesize 2,3,4,5-tetrahydropyridazin-3-one (XIV).

Preparation Method 3

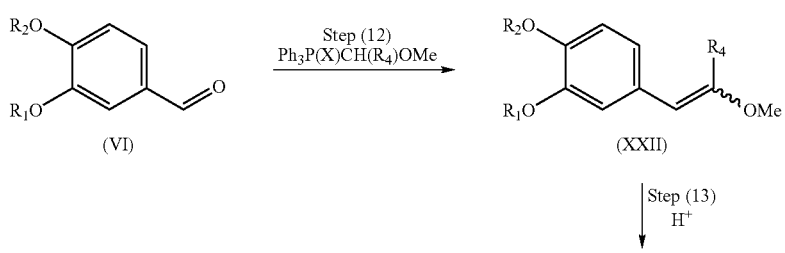

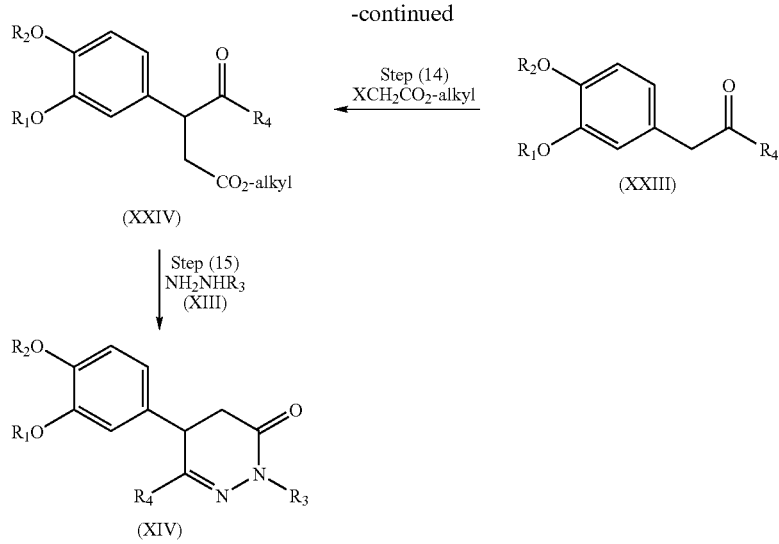

Compound (XIV) can also be synthesized according to the above method.

Step (12): The aldehyde derivative (VI) is derivatized to a vinyl ether (XXII) by the Wittig reaction.

Step (13): The vinyl ether (XXII) is hydrolyzed to synthesize a ketone derivative (an aldehyde derivative when $R_4$ is hydrogen) (XXIII).

Step (14): A halogenated acetic acid ester is reacted to the ketone derivative (an aldehyde derivative when $R_4$ is hydrogen) (XXIII) in the presence of a base to synthesize a 4-keto butyric acid ester (XXIV).

Step (15): In a method similar to step (5), the 4-keto butyrate (XXIV) and a hydrazine (XIII) are reacted to synthesize a 2,3,4,5-tetrahydropyridazin-3-one (XIV).

The starting substance used in the reaction scheme may be a commercially available compound or may be synthesized from a known compound in a known method. The ketone derivative (VI), a starting substance, may be prepared in a method described in the International Patent Publication WO94/10118 brochure.

When the compound of the present invention is used as a therapeutic agent, it may be administered alone or in combination with a pharmaceutically acceptable carrier. The composition may be determined based on the solubility and chemical properties of the compound, the administration route, the administration regimen etc.

For example, it may be orally administered in a dosage form such as a granule, a powder, a tablet, a pill, a hard capsule, a soft capsule, a syrup, an emulsion, a suspension and a solution, or it may be parenterally administered in a dosage form such as an injection (intravenous, intramuscular, subcutaneous), an ointment, a suppository, and an aerosol. Also, it may a powder for injection that is prepared immediately prior to use. Organic or inorganic solid or liquid carriers or diluents for pharmaceutical use suitable for oral, enteral, parenteral or local administration may be used together with the compound of the present invention. For example, in the case of an oral agent, an excipient such as glucose, corn starch and sucrose, a disintegrant such as carboxymethyl cellulose calcium and hydroxypropyl cellulose, a lubricant such as calcium stearate, magnesium stearate, talc, polyethylene glycol and a hydrogenated oil, a wetting agent such as hydroxypropyl cellulose, hydroxypropyl methyl cellulose, carboxymethyl cellulose, polyvinyl alcohol, gelatin and gum Arabic, and as needed a surfactant, a corrigent etc. may be used to prepare the desired dosage form.

Also in the case of a parenteral agent, a diluent such as water, ethanol, glycerin, propylene glycol, polyethylene glycol, agar and tragacanth gum may be used, and as needed, a dissolution adjuvant, a buffer, a preservative, a perfume, a colorant etc. may be used. The formulations may be prepared according to a standard method.

The clinical dosage when used in oral administration may generally be 0.01-1000 mg, preferably 0.01-100 mg, per day of the compound of the present invention for an adult, but the quantity may preferably be adjusted depending on the age, disease conditions, symptoms, the presence or absence of simultaneous administration etc. The above daily dosage of the agent (the compound of the present invention) may be administered once per day, or in two or three divided doses per day in appropriate intervals, or may be intermittently administered. When used as an injection, preferably the daily dose for an adult of 0.001-100 mg per day of the compound of the present invention may be continuously or intermittently administered.

EXAMPLES

The present invention will now be explained with reference to working examples and experimental examples, but the present invention is not limited to the following working examples or experimental examples as long as they are within the gist of the present invention.

Elution in column chromatography of Working Examples was performed under examination by thin layer chromatography (TLC). In TLC examination, Merck's 60F254 was used as the TLC plate, the solvent used as an elution solvent in column chromatography was used as a development solvent, and a UV detector was used in the detection method. Silica gel ($SiO_2$) for column used was silica gel PSQ60B or PSQ100B manufactured by Fuji Silysia Chemical Ltd. NMR spectra were recorded on JNM-AL400 manufactured by JEOL DATUM LTD. with tetramethylsilane as the internal or external standard. Chemical shift was expressed in terms of the δ value and the coupling constant in terms of Hz. Numerical values indicated in parentheses in mixed solvents represent the volume mixed ratio of each solvent. The % in the solution represents grams in 100 ml of the solvent. Symbols in Working Examples have the following meanings:
s: singlet
d: doublet
t: triplet
q: quartet
dd: double doublet
m: multiplet
br: broad
br s: broad singlet
J: coupling constant
HRMS: high resolution mass spectrum Example 1

Synthesis of 5-(3,4-dimethoxyphenyl)pyridazin-3-one (Table 1, Compound No. 1)

(1) Synthesis of 3,4-dimethoxy benzylidene malonic acid diethyl ester 3,4-dimethoxybenzaldehyde (Veratraldehyde) (9.13 g, 55 mM) was heated with malonic acid diethyl ester (8.00 g, 50 mM), acetic acid (0.29 ml) and piperidine (0.74 ml) in benzene (100 ml) in an apparatus equipped with a water separator (Dean-Stark tube) until 50 mM water was separated. After washing the benzene solution with water, it was dried over anhydrous magnesium sulfate. After drying, benzene was evaporated under reduced pressure to obtain a crude product (15.40 g). The crude product thus obtained is pure enough, and can be used in the subsequent reaction without further purification.

$^1$H-NMR (CDCl$_3$) δ: 1.33 (3H, t, J=7.32 Hz), 1.33 (3H, t, J=7.32 Hz), 3.87 (3H, s), 3.91 (3H, s), 4.29 (2H, q, J=7.32 Hz), 4.35 (2H, q, J=7.35 Hz), 6.86 (1H, d, J=8.30 Hz), 7.03 (1H, d, J=1.95 Hz), 7.09 (1H, dd, J=8.30, 1.95 Hz), 7.66 (1H, s).

(2) Synthesis of 3-(3,4-dimethoxyphenyl)-4,4-diethoxy-2-ethoxycarbonyl butyric acid ethyl ester A solution of methyl methylsulfinyl-methylsulfide (2.34 g, 18.81 M) in dry tetrahydrofuran (24 ml) was cooled to 0° C., and to this solution a solution of butyl lithium in hexane (18.81 mM) was added dropwise, which was stirred at the temperature as it was for 30 minutes. Then, the solution was cooled to −78° C., and a solution of 3,4-dimethoxybenzylidene malonic acid diethyl ester (5.00 g, 15.47 mM) in dry tetrahydrofuran (2 ml) was added. The solution obtained was gradually warmed to room temperature, was poured into an aqueous solution of ammonium chloride, extracted with diethylether, and after drying the organic extract over anhydrous magnesium sulfate, the solvent was evaporated under reduced pressure to obtain a crude product (6.70 g) of a brown oil of 3-(3,4-dimethoxyphenyl)-2-ethoxycarbonyl-4-methylsulfinyl-4-methylthio butyric acid ethyl ester. This was dissolved in dry ethanol (25 ml), and then ethyl orthoformate (3.09 g, 20.88 mM) and sulfuric acid (0.25 ml) were added and stirred at room temperature for 3 days. This solution was poured into an aqueous solution of sodium bicarbonate under cooling on ice, extracted with diethylether, and after the organic extract was dried, the solvent was evaporated under reduced pressure to obtain an oily crude product. The crude product was purified by flash chromatography (SiO$_2$: eluted with ethyl acetate). It was concentrated under reduced pressure and dried to obtain a yellow oil of 3-(3,4-dimethoxyphenyl)-4,4-diethoxy-2-ethoxycarbonyl butyric acid ethyl ester (5.08 g, yield 79.5%).

(3) Synthesis of 5-(3,4-dimethoxyphenyl)-2,3,4,5-tetrahydropyridazin-3-one 3-(3,4-dimethoxyphenyl)-4,4-diethoxy-2-ethoxycarbonyl butyric acid ethyl ester (3.07 g, 7.44 mM) and potassium hydroxide (3.41 g) were refluxed in ethanol (40 ml) for 4 hours. To this solution water was poured, acidified with concentrated hydrochloric acid, and extracted with diethylether. The organic extract was dried over anhydrous magnesium sulfate, and the solvent was evaporated under reduced pressure to obtain a brown oil of 3-(3,4-dimethoxyphenyl)-4,4-diethoxy butyric acid (1.98 g). The brown oil (1.98 g) thus obtained and hydrazine hydrate (0.90 ml) were added to a mixture of acetic acid (8.3 ml) and water (6.3 ml), refluxed for 5 hours, poured into an aqueous solution of sodium bicarbonate, extracted with methylene chloride, dried, and the solvent was evaporated under reduced pressure to obtain a yellow solid residue. The residue was purified with flash chromatography (SiO$_2$: eluted with a gradient of 60% ethyl acetate/hexane to 70% ethyl acetate/hexane). The solvent was evaporated under reduced pressure, and the residue was dried to obtain the pale yellow solid of title compound (0.92 g, yield 53.0%).

$^1$H-NMR (CDCl$_3$) δ: 2.63 (1H, dd, J=17.09, 11.23 Hz), 2.82 (1H, dd, J=17.09, 7.81 Hz), 3.81 (1H, ddd, J=11.23, 7.81, 2.44 Hz), 3.89 (3H, s), 3.89 (3H, s), 6.71 (1H, d, J=1.96 Hz), 6.77 (1H, dd, J=8.30, 1.96 Hz), 6.87 (1H, d, J=8.30 Hz), 7.18 (1H, d, J=2.44 Hz), 8.48 (1H, brs).

(4) Synthesis of 5-(3,4-dimethoxyphenyl)pyridazin-3-one 5-(3,4-dimethoxyphenyl)-2,3,4,5-tetrahydropyridazin-3-one (288 mg) was suspended in a mixed solvent of dimethyl sulfoxide (3 ml) and water (0.1 ml), to which N-bromosuccinimide (438 mg) was added under cooling on ice. After the addition was complete, the reaction temperature was raised to room temperature and stirred for 2 hours. The reaction mixture was poured into an ice-cold water and the deposit was filtered. The residue was purified with flash chromatography (SiO$_2$: eluted with ethyl acetate) to obtain the title compound (185 mg, yield 64.7%).

$^1$H-NMR (CDCl$_3$) δ: 10.39 (1H, s), 8.08 (1H, d, J=2.1 Hz), 7.20 (1H, dd, J=8.3, 2.2 Hz), 7.07 (1H, d, J=2.1 Hz), 7.02 (1H, d, J=2.2 Hz), 6.99 (1H, d, J=8.4 Hz), 3.95 (6H, s).

HRMS (EI): Found 232.0834; (Calcd. 232.0848).

Example 2

Synthesis of 5-(3-(cyclopropylmethyl)-4-methoxyphenyl)-2-methylpyridazin-3-one (Table 1, Compound No. 2)

Using a method similar to Working Example 1 (1)-(4), 3-(cyclopropylmethyl)-4-methoxybenzaldehyde was substituted for 3,4-dimethoxybenzaldehyde and methylhydrazine for hydrazine hydrate to obtain the title compound.

$^1$H-NMR (CDCl$_3$) δ: 8.02 (1H, d, J=2.2 Hz), 7.18 (1H, dd, J=8.4, 2.0 Hz), 7.07 (1H, d, J=2.0 Hz), 7.00 (1H, d, J=2.2 Hz), 6.97 (1H, d, J=8.4 Hz), 3.93 (3H, s), 3.91 (2H, d, J=7.0 Hz), 3.82 (3H, s), 1.40-1.31 (1H, m), 0.71-0.65 (2H, m), 0.41-0.36 (2H, m).

HRMS (EI): Found 286.1293; (Calcd. 286.1317).

Example 3

Synthesis of 5-(3-(cyclopentyloxy)-4-methoxyphenyl)-2-methylpyridazin-3-one (Table 1, Compound No. 3)

Using a method similar to Working Example 1 (1)-(4), 3-(cyclopentyloxy)-4-methoxybenzaldehyde was substituted for 3,4-dimethoxybenzaldehyde and methylhydrazine for hydrazine hydrate to obtain the title compound.

$^1$H-NMR (CDCl$_3$) δ: 8.02 (1H, d, J=2.1 Hz), 7.16 (1H, dd, J=8.4, 2.0 Hz), 7.07 (1H, d, J=2.0 Hz), 7.00 (1H, d, J=2.1 Hz), 6.95 (1H, d, J=8.3 Hz), 4.86-4.79 (1H, m), 3.90 (3H, s), 3.82 (3H, s), 2.03-1.80 (6H, m), 1.70-1.61 (2H, m).

Example 4

Synthesis of 5-(4-methoxy-3-(3-tetrahydrofuranyloxy)phenyl)pyridazin-3-one (Table 1, Compound No. 4)

Using a method similar to Working Example 1 (1)-(4), 4-methoxy-3-(3-tetrahydrofuranyloxy)benzaldehyde was substituted for 3,4-dimethoxybenzaldehyde to obtain the title compound.

$^1$H-NMR (CDCl$_3$) δ: 10.98 (1H, s), 8.07 (1H, d, J=1.7 Hz), 7.24 (1H, dd, J=8.4, 1.8 Hz), 7.06-6.99 (3H, m), 5.04-4.99 (1H, m), 4.09-3.91 (4H, m), 3.92 (3H, s), 2.25-2.20 (2H, m).

HRMS (EI): Found 288.1093; (Calcd. 288.1110).

Example 5

Synthesis of 5-(3-(cyclopentyloxy)-4-methoxyphenyl)pyridazin-3-one (Table 1, Compound No. 5)

Using a method similar to Working Example 1 (1)-(4), 3-(cyclopentyloxy)-4-methoxybenzaldehyde was substituted for 3,4-dimethoxybenzaldehyde to obtain the title compound.

$^1$H-NMR (CDCl$_3$) δ: 10.59 (1H, s), 8.07 (1H, d, J=1.8 Hz), 7.17 (1H, dd, J=8.4, 1.9 Hz), 7.08 (1H, d, J=1.8 Hz), 7.01 (1H, d, J=1.7 Hz), 6.97 (1H, d, J=8.4 Hz), 4.86-4.80 (1H, m), 3.91 (3H, s), 2.03-1.81 (6H, m), 1.69-1.61 (2H, m).

HRMS (EI): Found 286.1306; (Calcd. 286.1317).

Example 6

Synthesis of 5-(3-(cyclopentyloxy)-4-methoxyphenyl)-2-phenylpyridazin-3-one (Table 1, Compound No. 6)

Using a method similar to Working Example 1 (1)-(4), 3-(cyclopentyloxy)-4-methoxybenzaldehyde was substituted for 3,4-dimethoxybenzaldehyde and phenylhydrazine for hydrazine hydrate to obtain the title compound.

$^1$H-NMR (CDCl$_3$) δ: 8.19 (1H, d, J=2.2 Hz), 7.69-7.64 (2H, m), 7.50 (2H, dd, J=7.4, 7.4 Hz), 7.41 (1H, dd, J=7.4, 7.4 Hz), 7.23 (1H, dd, J=8.4, 2.1 Hz), 7.14 (1H, d, J=2.2 Hz), 7.13 (1H, d, J=2.3 Hz), 6.99 (1H, d, J=8.4 Hz), 4.87-4.82 (1H, m), 3.92 (3H, s), 2.03-1.82 (6H, m), 1.69-1.62 (2H, m).

HRMS (EI): Found 362.1630; (Calcd. 362.1630).

Example 7

Synthesis of 5-(3,4-dimethoxyphenyl-2-phenylpyridazin-3-one (Table 1, Compound No. 7)

Using a method similar to Working Example 1 (1)-(4), phenylhydrazine was substituted for hydrazine hydrate to obtain the title compound.

$^1$H-NMR (CDCl$_3$) δ: 8.20 (1H, d, J=2.3 Hz), 7.68-7.64 (2H, m), 7.53-7.47 (2H, m), 7.43-7.39 (1H, m), 7.28-7.25 (1H, m), 7.14 (2H, dd, J=8.1, 2.2 Hz), 7.00 (1H, d, J=8.4 Hz), 3.97 (3H, s), 3.96 (3H, s).

HRMS (EI): Found 308.1151; (Calcd. 308.1161).

Example 8

Synthesis of 5-(3-(cyclopentyloxy)-4-ethoxyphenyl)-2-methylpyridazin-3-one (Table 1, Compound No. 8)

Using a method similar to Working Example 1 (1)-(4), 3-(cyclopentyloxy)-4-ethoxybenzaldehyde was substituted for 3,4-dimethoxybenzaldehyde and phenylhydrazine for hydrazine hydrate to obtain the title compound.

$^1$H-NMR (CDCl$_3$) δ: 8.02 (1H, d, J=2.1 Hz), 7.14 (1H, dd, J=8.3, 2.1 Hz), 7.08 (1H, d, J=2.2 Hz), 7.00 (1H, d, J=2.2 Hz), 6.95 (1H, d, J=8.3 Hz), 4.84-4.79 (1H, m), 4.12 (2H, q, J=7.0 Hz), 3.82 (3H, s), 1.95-1.80 (6H, m), 1.68-1.60 (2H, m), 1.46 (3H, t, J=7.1 Hz).

HRMS (EI): Found 314.1628; (Calcd. 314.1630).

Example 9

Synthesis of 5-(4-methoxy-3-(tetrahydrofuranyloxy)phenyl)-2-phenylpyridazin-3-one (Table 1, Compound No. 9)

Using a method similar to Working Example 1 (1)-(4), 4-methoxy-3-(3-tetrahydrofuranyloxy)benzaldehyde was substituted for 3,4-dimethoxybenzaldehyde and phenylhydrazine for hydrazine hydrate to obtain the title compound.

$^1$H-NMR (CDCl$_3$) δ: 8.18 (1H, d, J=2.3 Hz), 7.68-7.64 (2H, m), 7.53-7.48 (2H, m), 7.43-7.39 (1H, m), 7.29 (1H, dd, J=8.4, 2.2 Hz), 7.12 (1H, d, J=2.3 Hz), 7.10 (1H, d, J=2.3 Hz), 7.02 (1H, d, J=8.4 Hz), 5.05-5.01 (1H, m), 4.09-3.94 (4H, m), 3.93 (3H, s), 2.26-2.21 (2H, m).

HRMS (EI): Found 364.1413; (Calcd. 364.1423).

Example 10

Synthesis of 5-(3-(cyclopropylmethoxy)-4-methoxyphenyl)-2-phenylpyridazin-3-one (Table 1, Compound No. 10)

Using a method similar to Working Example 1 (1)-(4), 3-(cyclopropylmethoxy)-4-methoxybenzaldehyde was substituted for 3,4-dimethoxybenzaldehyde and phenylhydrazine for hydrazine hydrate to obtain the title compound.

$^1$H-NMR (CDCl$_3$) δ: 8.19 (1H, d, J=2.3 Hz), 7.68-7.64 (2H, m), 7.53-7.47 (2H, m), 7.42-7.38 (1H, m), 7.27-7.24 (1H, m), 7.14 (1H, d, J=2.2 Hz), 7.12 (1H, d, J=2.3 Hz), 7.00 (1H, d, J=8.4 Hz), 3.95 (3H, s), 3.93 (2H, d, J=7.0 Hz), 1.41-1.33 (1H, m), 0.72-0.67 (2H, m), 0.42-0.38 (2H, m).

HRMS (EI): Found 348.1463; (Calcd. 348.1474).

Example 11

Synthesis of 5-(3-(cyclopentyloxy)-4-(difluoromethoxy)phenyl)-2-methylpyridazin-3-one (Table 1, Compound No. 11)

Using a method similar to Working Example 1 (1)-(4), 3-(cyclopentyloxy)-4-(difluoromethoxy)benzaldehyde was substituted for 3,4-dimethoxybenzaldehyde and methylhydrazine for hydrazine hydrate to obtain the title compound.

¹H-NMR (CDCl₃) δ: 7.99 (1H, d, J=2.2 Hz), 7.26 (1H, d, J=8.7 Hz), 7.12-7.09 (2H, m), 7.02 (1H, d, J=2.3 Hz), 6.59 (1H, t, J=75.0 Hz), 4.88-4.84 (1H, m), 3.84 (3H, s), 1.98-1.78 (6H, m), 1.72-1.64 (2H, m).
HRMS (EI): Found 336.1277; (Calcd. 336.1286).

Example 12

Synthesis of 5-(4-methoxy-3-(3-tetrahydrofuranyloxy)phenyl)-2-methylpyridazin-3-one (Table 1, Compound No. 12)

Using a method similar to Working Example 1 (1)-(4), 4-methoxy-3-(3-tetrahydrofuranyloxy)benzaldehyde was substituted for 3,4-dimethoxybenzaldehyde and methylhydrazine for hydrazine hydrate to obtain the title compound.
¹H-NMR (CDCl₃) δ: 8.01 (1H, d, J=2.2 Hz), 7.22 (1H, dd, J=8.4, 2.2 Hz), 7.03 (1H, d, J=2.2 Hz), 6.99 (1H, d, J=2.3 Hz), 6.99 (1H, d, J=8.3 Hz), 5.03-4.98 (1H, m), 4.08-3.93 (4H, m), 3.91 (3H, s), 3.82 (3H, s), 2.25-2.19 (2H, m).
HRMS (EI): Found 302.1261; (Calcd. 302.1267).

Example 13

Synthesis of 5-(3-(2-indanyloxy)-4-methoxyphenyl)-2-methylpyridazin-3-one (Table 1, Compound No. 13)

Using a method similar to Working Example 1 (1)-(4), 3-(2-indanyloxy)-4-methoxybenzaldehyde was substituted for 3,4-dimethoxybenzaldehyde and methylhydrazine for hydrazine hydrate to obtain the title compound.
¹H-NMR (CDCl₃) δ: 8.03 (1H, d, J=2.4 Hz), 7.26-7.18 (5H, m), 7.13 (1H, d, J=2.2 Hz), 7.02 (1H, d, J=2.4 Hz), 6.98 (1H, d, J=8.5 Hz), 5.26-5.21 (1H, m), 3.88 (3H, s), 3.83 (3H, s), 3.41 (2H, dd, J=16.6, 6.6 Hz), 3.27 (2H, dd, J=16.6, 3.7 Hz).
HRMS (EI): Found 348.1484; (Calcd. 348.1474).

Example 14

Synthesis of (R)-5-(4-methoxy-3-(3-tetrahydrofuranyloxy)phenyl)-2-methylpyridazin-3-one (Table 1, Compound No. 14)

Using a method similar to Working Example 1 (1)-(4), (R)-4-methoxy-3-(3-tetrahydrofuranyloxy)benzaldehyde was substituted for 3,4-dimethoxybenzaldehyde and methylhydrazine for hydrazine hydrate to obtain the title compound.
¹H-NMR (CDCl₃) δ: 8.01 (1H, d, J=2.3 Hz), 7.22 (1H, dd, J=8.4, 2.2 Hz), 7.04 (1H, d, J=2.2 Hz), 7.00-6.98 (2H, m), 5.02-4.99 (1H, m), 4.08-3.93 (4H, m), 3.91 (3H, s), 3.82 (3H, s), 2.24-2.19 (2H, m).

Example 15

Synthesis of (R)-5-(4-methoxy-3-(3-tetrahydrofuranyloxy)phenyl)-2-phenylpyridazin-3-one (Table 1, Compound No. 15)

Using a method similar to Working Example 1 (1)-(4), (R)-4-methoxy-3-(3-tetrahydrofuranyloxy)benzaldehyde was substituted for 3,4-dimethoxybenzaldehyde and phenylhydrazine for hydrazine hydrate to obtain the title compound.
¹H-NMR (CDCl₃) δ: 8.18 (1H, d, J=2.3 Hz), 7.68-7.64 (2H, m), 7.52-7.48 (2H, m), 7.43-7.39 (1H, m), 7.29 (1H, dd, J=8.4, 2.2 Hz), 7.12 (1H, d, J=2.3 Hz), 7.10 (1H, d, J=2.2 Hz), 7.02 (1H, d, J=8.4 Hz), 5.05-5.01 (1H, m), 4.09-3.94 (4H, m), 3.93 (3H, s), 2.26-2.21 (2H, m).

Example 16

Synthesis of (S)-5-(4-methoxy-3-(3-tetrahydrofuranyloxy)phenyl)-2-methylpyridazin-3-one (Table 1, Compound No. 16)

Using a method similar to Working Example 1 (1)-(4), (S)-4-methoxy-3-(3-tetrahydrofuranyloxy)benzaldehyde was substituted for 3,4-dimethoxybenzaldehyde and methylhydrazine for hydrazine hydrate to obtain the title compound.
¹H-NMR (CDCl₃) δ: 8.01 (1H, d, J=2.2 Hz), 7.22 (1H, dd, J=8.4, 2.1 Hz), 7.04 (1H, d, J=2.1 Hz), 6.99 (1H, d, J=2.3 Hz), 6.99 (1H, d, J=8.4 Hz), 5.02-4.99 (1H, m), 4.08-3.93 (4H, m), 3.91 (3H, s), 3.82 (3H, s), 2.25-2.19 (2H, m).

Example 17

Synthesis of (S)-5-(4-methoxy-3-(3-tetrahydrofuranyloxy)phenyl)-2-phenylpyridazin-3-one (Table 1, Compound No. 17)

Using a method similar to Working Example 1 (1)-(4), (S)-4-methoxy-3-(3-tetrahydrofuranyloxy)benzaldehyde was substituted for 3,4-dimethoxybenzaldehyde and phenylhydrazine for hydrazine hydrate to obtain the title compound.
¹H-NMR (CDCl₃) δ: 8.17 (1H, d, J=2.2 Hz), 7.66 (2H, d, J=7.4 Hz), 7.53-7.48 (2H, m), 7.43-7.39 (1H, m), 7.29 (1H, dd, J=8.4, 2.1 Hz), 7.11 (1H, d, J=2.3 Hz), 7.10 (1H, d, J=2.1 Hz), 7.02 (1H, d, J=8.2 Hz), 5.04-5.01 (1H, m), 4.09-3.94 (4H, m), 3.93 (3H, s), 2.26-2.21 (2H, m).

Example 18

Synthesis of 5-(3-(cyclopentyloxy)-4-methoxyphenyl)-2-(3-pentyl)pyridazin-3-one (Table 1, Compound No. 18)

To 5-(3-(cyclopentyloxy)-4-methoxyphenyl)pyridazin-3-one prepared in Working Example 5, sodium hydride was added and stirred for 1 hour. Then, 3-pentylbromide dissolved in dimethylformamide was added dropwise and stirred for 18 hours. The reaction mixture was poured into ice-cold water and extracted with ethyl acetate. The organic layer was washed with brine, and then dried over anhydrous sodium sulfate. The residue that had been filtered and concentrated was purified by flash chromatography to obtain the title compound.
¹H-NMR (CDCl₃) δ: 8.11 (1H, d, J=2.3 Hz), 7.18 (1H, dd, J=8.4, 2.1 Hz), 7.10 (1H, d, J=2.1 Hz), 7.00 (1H, d, J=2.3 Hz), 6.96 (1H, d, J=8.4 Hz), 5.03-4.96 (1H, m), 4.85-4.80 (1H, m), 3.91 (3H, s), 2.01-1.63 (12H, m), 0.85 (6H, t, J=7.4 Hz).
HRMS (EI): Found 356.2088; (Calcd. 356.2100).

Example 19

Synthesis of 5-(3-(cyclopentyloxy)-4-methoxyphenyl)-2-(2-quinolylmethyl)pyridazin-3-one (Table 1, Compound No. 19)

Using a method similar to Working Example (18), 2-(chloromethyl)quinoline was substituted for 3-pentylbromide to obtain the title compound.
¹H-NMR (CDCl₃) δ: 8.14-8.09 (3H, m), 7.79 (1H, d, J=8.4 Hz), 7.73-7.68 (1H, m), 7.55-7.50 (1H, m), 7.42 (1H, d, J=8.4

Hz), 7.18 (1H, dd, J=8.3, 2.2 Hz), 7.09 (1H, d, J=2.2 Hz), 7.08 (1H, d, J=2.3 Hz), 6.96 (1H, d, J=8.4 Hz), 5.71 (2H, s), 4.84-4.80 (1H, m), 3.90 (3H, s), 2.00-1.81 (6H, m), 1.68-1.61 (2H, m).

HRMS (EI): Found 427.1889; (Calcd. 427.1896).

Example 20

Synthesis of 5-(3-(cyclopentyloxy)-4-methoxyphenyl)-2,6-dimethylpyridazin-3-one (Table 1, Compound No. 20)

Using a method similar to Working Example 1 (1)-(4), 3-(cyclopentyloxy)-4-methoxybenzaldehyde was substituted for 3,4-dimethoxybenzaldehyde, methyl(1-methylsulfinyl)ethyl)sulfine for methyl methylsulfinyl-methylsulfide, and methylhydrazine for hydrazine hydrate to obtain the title compound.

$^1$H-NMR (CDCl$_3$) δ: 6.92 (1H, d, J=8.2 Hz), 6.84 (1H, dd, J=8.2, 2.1 Hz), 6.79 (1H, d, J=2.1 Hz), 6.78 (1H, s), 4.79-4.74 (1H, m), 3.89 (3H, s), 3.79 (3H, s), 2.27 (3H, s), 1.95-1.82 (6H, m), 1.65-1.60 (2H, m).

HRMS (EI): Found 314.1637; (Calcd. 314.1630).

Example 21

Synthesis of 5-(3-(cyclopentyloxy)-4-methoxyphenyl)-2-((2-benzothiazolone)-3-ylmethyl)pyridazin-3-one (Table 1, Compound No. 21)

Using a method similar to Working Example (18), 3-(chrolomethyl)-2-benzothiazolone was substituted for 3-pentylbromide to obtain the title compound.

$^1$H-NMR (CDCl$_3$) δ: 8.11 (1H, d, J=2.3 Hz), 7.54 (1H, d, J=8.2 Hz), 7.42 (1H, dd, J=7.8, 0.9 Hz), 7.33-7.28 (1H, m), 7.18 (1H, td, J=7.6, 1.1 Hz), 7.13-7.10 (1H, m), 7.02 (1H, d, J=2.2 Hz), 6.99 (1H, d, J=2.3 Hz), 6.93 (1H, d, J=8.5 Hz), 6.32 (2H, s), 4.81-4.76 (1H, m), 3.90 (3H, d, J=6.6 Hz), 1.98-1.81 (6H, m), 1.65-1.61 (2H, m).

HRMS (EI): Found 449.1397; (Calcd. 449.1409).

TABLE 1

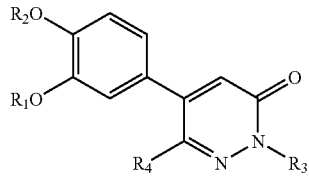

| Compound No. | R$^1$ | R$^2$ | R$^3$ | R$^4$ |
|---|---|---|---|---|
| 1 | Me | Me | H | H |
| 2 | cyclopropylmethyl | Me | Me | H |
| 3 | cyclopentyl | Me | Me | H |
| 4 | tetrahydrofuran-3-yl | Me | H | H |
| 5 | cyclopentyl | Me | H | H |
| 6 | cyclopentyl | Me | Ph | H |
| 7 | Me | Me | Ph | H |
| 8 | cyclopentyl | Et | Me | H |
| 9 | tetrahydrofuran-3-yl | Me | Ph | H |
| 10 | cyclopropylmethyl | Me | Ph | H |
| 11 | cyclopentyl | CHF$_2$ | Me | H |
| 12 | tetrahydrofuran-3-yl | Me | Me | H |
| 13 | indan-2-yl | Me | Me | H |
| 14 | (R)-tetrahydrofuran-3-yl | Me | Me | H |
| 15 | (R)-tetrahydrofuran-3-yl | Me | Ph | H |
| 16 | (S)-tetrahydrofuran-3-yl | Me | Me | H |
| 17 | (S)-tetrahydrofuran-3-yl | Me | Ph | H |
| 18 | cyclopentyl | Me | isobutyl | H |

TABLE 1-continued

Structure:

R₂O—, R₁O— on phenyl, attached to pyridazinone ring with R₄ at position, N-R₃, C=O

| Compound No. | R¹ | R² | R³ | R⁴ |
|---|---|---|---|---|
| 19 | cyclopentyl | Me | 2-ethylquinolinyl | H |
| 20 | cyclopentyl | Me | Me | Me |
| 21 | cyclopentyl | Me | 3-ethyl-2-oxo-benzothiazolyl | H |

Example 22

Preparation of Tablets 5-(3-cyclopentyloxy-4-methoxyphenyl)-2,3,4,5-tetrahydropyridazin-3-one (Table 1, Compound No. 3) (30 g), lactose (253 g), corn starch (63 g), low-substituted hydroxypropyl cellulose (40 g), and calcium stearate (4 g) were mixed, and compressed in a standard method so that each tablet contains 10 mg of the above compound.

Example 23

Preparation of Capsules 5-(3-cyclopentyloxy-4-methoxyphenyl)-2,3,4,5-tetrahydropyridazin-3-one (Table 1, Compound No. 3) (30 g), lactose (260 g), corn starch (66 g), and calcium stearate (4 g) were mixed, and then filled in gelatin capsules in a standard method so that each capsule contains 10 mg of the above compound.

Biological Experiment Example 1

The Activity of Inhibiting PAI-1 Production Using Airway Epithelial Cells

The effect of a compound on PAI-1 production activity using airway epithelial cells was examined. This reflects PAI-1 concentration in the lung tissue related to fibrosis (lung).

The effect on the amount of PAI-1 produced using human airway epithelial cells (BEAS-2B) was examined. After 0.1 ml each of BEAS-2B cells prepared at $2 \times 10^6$ cells/ml was added to a collagen I-coated 96-well plate, preincubated for 24 hours, 0.1 ml of a medium containing 10 μM TGF-β was added thereto and incubated for 24 hours, the amount of PAI-1 in the culture supernatant was determined using an ELISA kit. The test substance was dissolved in dimethyl sulfoxide (final concentration, 0.1% or less), and was prepared at 0.2, 1, 5 and 25 μM using a phosphate buffer, and added after preculturing. The activity of inhibiting PAI-1 production of the compound of the present invention was expressed in terms of the IC50 value and shown in Table 2.

TABLE 2

| Compound No. | PAI-1 production-inhibiting activity, IC50(μM) |
|---|---|
| 1 | 14.1 |
| 2 | 16.8 |
| 3 | 5.8 |
| 4 | 8.4 |
| 12 | 4.0 |
| 16 | 23.2 |

Biological Experiment Example 2

The Activity of Inhibiting PAI-1 Production on the Bleomycin-Induced Pulmonary Fibrosis Model It has been reported that bleomycin administration into the trachea leads to pulmonary fibrosis. Its pathological findings including the hypertrophy and fibrosis of the alveolar wall, increased inflammatory cells, the increased amount of hydroxyproline etc. are similar to clinical idiopathic pulmonary fibrosis, and it has been often used as an experimental model of pulmonary fibrosis (Biochem. Biophys. Res. Comm. 288, 747 (2001)). To C57BL/6 mice (6-week-old, female), bleomycin hydrochloride (Bleo: NIPPON KAYAKU CO., LTD) (6 mg/kg, 25 μl/animal) was injected into the bronchus together with 500 μl of compressed air. Three weeks after administration into the trachea, the amount of hydroxyproline in the lung was determined. 0.3 mg/kg of the test substance was suspended in 0.5% carboxymethyl cellulose sodium, and orally administered once daily. The effect of the compound of the present invention was expressed in the inhibition percentage relative to the increased amount of lung hydroxyproline of the solvent-administration group, and shown in Table 3.

TABLE 3

| Compound No. | Inhibition percentage relative to the increased amount of pulmonary hydroxyproline (%) |
|---|---|
| 2 | 66 |
| 3 | 68 |
| 6 | 84 |
| 9 | 117 |
| 19 | 132 |

Biological Experiment Example 3

Acute Toxicity Study

The compounds of the present invention No. 1 to No. 21 were suspended in physiological saline containing 0.5% carboxymethyl cellulose sodium, which was then intraperitoneally administered to male ddY mice, and the next day the animals were checked whether they were alive or dead. No compounds caused death at the dosage of 30 mg/kg.

Industrial Applicability

The compound of the present invention has an excellent activity of inhibiting the production of plasminogen activator inhibitor-1, and, due to its fibrinolytic effect, is useful for preventing and/or treating tissue fibrinosis diseases such as pulmonary fibrosis and renal fibrosis, and diseases caused by pathological blood clots such as ischemic heart diseases (myocardial infarction, angina), intraatrial thrombus, pulmonary embolism and deep venous thrombosis.

The invention claimed is:
1. A compound represented by the following formula (I):

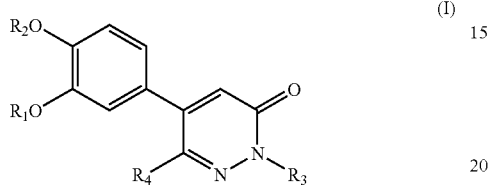

wherein,
$R_1$ represents:
a $C_1$-$C_8$ alkyl group optionally having one or more than one substituent which is selected from the group consisting of a halogen atom, a hydroxy group, a nitro group, a cyano group, an amino group, a carboxyl group, an alkyl group, a cycloalkyl group optionally having as a substituent one or more than one phenyl group or alkyl group, a haloalkyl group, a carbamoyl group optionally having one or more than one alkyl group substituent on the nitrogen atom, an alkoxy group, an alkoxycarbonyl group, an acyl group, a monocyclic or fused polycyclic aryl group, an oxyranyl group, an aziridinyl group, an oxetanyl group, a thietanyl group, a thioranyl group, a thiomorpholinyl group, a pyrrolidinyl group, a pyrrolinyl group, an imidazolidinyl group, an imidazolinyl group, a tetrahydrofuryl group, a pyrazolidinyl group, a pyrazolinyl group, a pyranyl group, a tetrahydropyranyl group, a piperazinyl group, a morpholinyl group, a piperidinyl group, an indolinyl group, an isoindolinyl group, a dihydrobenzofuranyl group, and an oxobenzothiazolinyl group;

a $C_3$-$C_7$ cycloalkyl group optionally having one or more than one of the above substituents;

an oxyranyl group, an aziridinyl group, an oxetanyl group, a thietanyl group, a thioranyl group, a thiomorpholinyl group, a pyrrolidinyl group, a pyrrolinyl group, an imidazolidinyl group, an imidazolinyl group, a tetrahydrofuryl group, a pyrazolidinyl group, a pyrazolinyl group, a pyranyl group, a tetrahydropyranyl group, a piperazinyl group, a morpholinyl group, or a piperidinyl group, that may have one or more than one of the above substituents; or an indanyl group, $R_2$ represents a $C_1$-$C_4$ alkyl group or a $C_1$-$C_4$ haloalkyl group, and $R_3$ represents:
a hydrogen atom,
a $C_1$-$C_8$ alkyl group optionally having one or more than one substituent which is selected from the group consisting of a halogen atom, a hydroxy group, a nitro group, a cyano group, an amino group, a carboxyl group, an alkyl group, a cycloalkyl group optionally having as a substituent one or more than one phenyl group or alkyl group, a haloalkyl group, a carbamoyl group optionally having one or more than one alkyl group substituent on the nitrogen atom, an alkoxy group, an alkoxycarbonyl group, an acyl group, a monocyclic or fused polycyclic aryl group, an oxyranyl group, an aziridinyl group, an oxetanyl group, a thietanyl group, a thioranyl group, a thiomorpholinyl group, a pyrrolidinyl group, a pyrrolinyl group, an imidazolidinyl group, an imidazolinyl group, a tetrahydrofuryl group, a pyrazolidinyl group, a pyrazolinyl group, a pyranyl group, a tetrahydropyranyl group, a piperazinyl group, a morpholinyl group, a piperidinyl group, an indolinyl group, an isoindolinyl group, a dihydrobenzofuranyl group, and an oxobenzothiazolinyl group;

a $C_3$-$C_7$ cycloalkyl group;

an oxyranyl group, an aziridinyl group, an oxetanyl group, a thietanyl group, a thioranyl group, a thiomorpholinyl group, a pyrrolidinyl group, a pyrrolinyl group, an imidazolidinyl group, an imidazolinyl group, a tetrahydrofuryl group, a pyrazolidinyl group, a pyrazolinyl group, a pyranyl group, a tetrahydropyranyl group, a piperazinyl group, a morpholinyl group, a piperidinyl group, a monocyclic or fused polycyclic aryl group, a thiazolyl group, a thienyl group, a furyl group, an isothiazolyl group, an oxazolyl group, an isoxazolyl group, a pyrrolyl group, an imidazolyl group, a furazanyl group, a pyrazolyl group, a pyridyl group, a pyrazinyl group, a pyrimidinyl group, a pyridazinyl group, a triazinyl group, a quinolyl group, an isoquinolyl group, an indolyl group, an isoindolyl group, an indolidinyl group, an indazolyl group, a phthalazinyl group, a naphthilidinyl group, a quinoxalinyl group, a quinazolinyl group, a prinyl group, a pteridinyl group, a synnolinyl group, a chromenyl group, a benzofuranyl group, a benzooxazolyl group, a benzisoxazolyl group, a benzothiazolyl group, a benzisothiazolyl group, or a benzimidazolyl group, and $R_4$ represents a hydrogen atom or a $C_1$-$C_6$ alkyl group or
an optical isomer thereof, or a pharmaceutically acceptable salt thereof, or a hydrate or solvate thereof.

2. The compound according to claim 1
wherein, $R_1$ represents:
a $C_1$-$C_8$ alkyl group optionally having one or more than one substituent which is selected from the group consisting of fluorine, chlorine, bromine, iodine, a hydroxy group, a nitro group, a cyano group, an amino group, a carboxyl group, a $C_1$-$C_6$ alkyl group, a $C_3$-$C_7$ cycloalkyl group optionally having as a substituent one or more than one phenyl group or a $C_1$-$C_6$ alkyl group, a $C_1$-$C_6$ haloalkyl group, a carbamoyl group optionally having one or more than one $C_1$-$C_4$ alkyl group substituent on the nitrogen atom, a $C_1$-$C_6$ alkoxy group, a $C_1$-$C_6$ alkoxycarbonyl group, a $C_1$-$C_6$ acyl group, a 6-10-membered monocyclic or a fused polycyclic aryl group, an oxyranyl group, an aziridinyl group, an oxetanyl group, a thietanyl group, a thioranyl group, a thiomorpholinyl group, a pyrrolidinyl group, a pyrrolinyl group, an imidazolidinyl group, an imidazolinyl group, a tetrahydrofuryl group, a pyrazolidinyl group, a pyrazolinyl group, a pyranyl group, a tetrahydropyranyl group, a piperazinyl group, a morpholinyl group, a piperidinyl group, an indolinyl group, an isoindolinyl group, a dihydrobenzofuranyl group, an oxobenzothiazolinyl group, a thiazolyl group, a thienyl group, a furyl group, an isothiazolyl group, an oxazolyl group, an isoxazolyl group, a pyrrolyl group, a imidazolyl group, a furazanyl group, a pyrazolyl group, a pyridyl group, a pyrazinyl group, a pyrimidinyl group, a pyridazinyl group, a triazinyl group, a quinolyl group, an isoquinolyl group, an indolyl group, an isoindolyl group, an indolidinyl group, an indazolyl group, a phthalazinyl group, a naphthilidinyl group, a quinoxalinyl group, a quinazolinyl group, a prinyl group, a pteridinyl group, a synnolinyl group, a chromenyl group, a benzofuranyl group, a benzooxazolyl group, a benzisoxazolyl group, a benzothiazolyl group, a benzisothiazolyl group, and a benzimidazolyl group;

a $C_3$-$C_7$ cycloalkyl group, optionally having one or more than one of the above substituents;

an oxyranyl group, an aziridinyl group, an oxetanyl group, a thietanyl group, a thioranyl group, a thiomorpholinyl group, a pyrrolidinyl group, a pyrrolinyl group, an imidazolidinyl group, an imidazolinyl group, a tetrahydrofuryl group, a pyrazolidinyl group, a pyrazolinyl group, a pyranyl group, a tetrahydropyranyl group, a piperazinyl group, a morpholinyl group, or a piperidinyl group, optionally having one or more than one of the above substituent; or an indanyl group, $R_2$ represents a $C_1$-$C_4$ alkyl group or a $C_1$-$C_4$ haloalkyl group having as a substituent a halogen atom which is selected from the group consisting of fluorine, chlorine, bromine, and iodine, $R_3$ represents:

a hydrogen atom, a $C_1$-$C_8$ alkyl group optionally having one or more than one substituent which is selected from the group consisting of fluorine, chlorine, bromine, iodine, a hydroxy group, a nitro group, a cyano group, an amino group, a carboxyl group, a $C_1$-$C_6$ alkyl group, a $C_3$-$C_7$ cycloalkyl group optionally having as a substituent one or more than one phenyl group or a $C_1$-$C6$ alkyl group, a $C_1$-$C_6$ haloalkyl group, a carbamoyl group optionally having as a substituent one or more than one $C_1$-$C_4$ alkyl group on the nitrogen atom, a $C_1$-$C_6$ alkoxy group, a $C_1$-$C_6$ alkoxycarbonyl group, a $C_1$-$C_6$ acyl group, a 6-10-membered monocyclic or fused polycyclic aryl group, an oxyranyl group, an aziridinyl group, an oxetanyl group, a thietanyl group, a thioranyl group, a thiomorpholinyl group, a pyrrolidinyl group, a pyrrolinyl group, an imidazolidinyl group, an imidazolinyl group, a tetrahydrofuryl group, a pyrazolidinyl group, a pyrazolinyl group, a pyranyl group, a tetrahydropyranyl group, a piperazinyl group, a morpholinyl group, a piperidinyl group, an indolinyl group, an isoindolinyl group, a dihydrobenzofuranyl group, an oxobenzothiazolinyl group, a thiazolyl group, a thienyl group, a furyl group, an isothiazolyl group, an oxazolyl group, an isoxazolyl group, a pyrrolyl group, a imidazolyl group, a furazanyl group, a pyrazolyl group, a pyridyl group, a pyrazinyl group, a pyrimidinyl group, a pyridazinyl group, a triazinyl group, a quinolyl group, an isoquinolyl group, an indolyl group, an isoindolyl group, an indolidinyl group, an indazolyl group, a phthalazinyl group, a naphthilidinyl group, a quinoxalinyl group, a quinazolinyl group, a prinyl group, a pteridinyl group, a synnolinyl group, a chromenyl group, a benzofuranyl group, a benzooxazolyl group, a benzisoxazolyl group, a benzothiazolyl group, a benzisothiazolyl group, and a benzimidazolyl group;

a $C_3$-$C_7$ cycloalkyl group;

an oxyranyl group, an aziridinyl group, an oxetanyl group, a thietanyl group, a thioranyl group, a thiomorpholinyl group, a pyrrolidinyl group, a pyrrolinyl group, an imidazolidinyl group, an imidazolinyl group, a tetrahydrofuryl group, a pyrazolidinyl group, a pyrazolinyl group, a pyranyl group, a tetrahydropyranyl group, a piperazinyl group, a morpholinyl group, a piperidinyl group, a 6-10-membered monocyclic or fused polycyclic aryl group, a thiazolyl group, a thienyl group, a furyl group, an isothiazolyl group, an oxazolyl group, an isoxazolyl group, a pyrrolyl group, a imidazoly group, a furazanyl group, a pyrazolyl group, a pyridyl group, a pyrazinyl group, a pyrimidinyl group, a pyridazinyl group, a triazinyl group, a quinolyl group, an isoquinolyl group, an indolyl group, an isoindolyl group, an indolidinyl group, an indazolyl group, a phthalazinyl group, a naphthilidinyl group, a quinoxalinyl group, a quinazolinyl group, a prinyl group, a pteridinyl group, a synnolinyl group, a chromenyl group, a benzofuranyl group, a benzooxazolyl group, a benzisoxazolyl group, a benzothiazolyl group, a benzisothiazolyl group, or a benzimidazolyl group, and $R_4$ represents a hydrogen atom or a methyl group.

3. The compound according to claim 1
wherein, $R_1$ represents:
a $C_1$-$C_8$ alkyl group;
a $C_1$-$C_5$ alkyl group having one or more than one phenyl group or a furyl group as a substituent;
a $C_1$-$C_5$ alkyl group having as a substituent one or more than one $C_3$-$C_7$ cycloalkyl group optionally having as a substituent one or more than one phenyl group or a $C_1$-$C_3$ alkyl group;
a $C_4$-$C_6$ cycloalkyl group optionally having one or more than one substituent which is selected from the group consisting of a methyl group and a hydroxy group;
a thioranyl group, a thiomorpholinyl group, a pyrrolidinyl group, a pyrrolinyl group, an imidazolidinyl group, an imidazolinyl group, a tetrahydrofuryl group, a pyrazolidinyl group, a pyrazolinyl group, a pyranyl group, a tetrahydropyranyl group, a piperazinyl group, a morpholinyl group, a piperidinyl group or an indanyl group, $R_2$ represents a methyl group, an ethyl group, a difluoromethyl group or a trifluoromethyl group, $R_3$ represents a hydrogen atom; a $C_1$-$C_8$ alkyl group; a phenyl group; a $C_1$-$C_2$ alkyl group having as a substituent a phenyl group; a quinolyl group; an oxobenzothiazolinyl group; or a pyridyl group, and $R_4$ represents a hydrogen atom or a methyl group.

4. The compound according to claim 1
wherein, $R_1$ is a methyl group, a butyl group, an isobutyl group, a neopentyl group, a $C_1$-$C_5$ alkyl group having a phenyl group as a substituent, a cyclopentyl group, a cyclohexyl group, a cyclopropylmethyl group, a cyclobutylmethyl group, a (1-methylcyclopropyl)methyl group, a (1-phenylcyclopropyl)methyl group, a tetrahydrofuryl group, a tetrahydropyranyl group, a 2-ethylbutyl group or an indanyl group, $R_2$ is a methyl group, an ethyl group, a difluoromethyl group or a trifluoromethyl group, $R_3$ is a hydrogen atom, a methyl group, an ethyl group, a 3-pentyl group, a phenyl group, a benzyl group, a quinolylmethyl group or an oxobenzothiazolinylmethyl group, and $R_4$ is a hydrogen atom or a methyl group.

5. The compound according to claim 1
wherein, $R_1$ is a methyl group, a cyclopentyl group, a cyclopropylmethyl group, a 3-tetrahydrofuryl group or a 2-indanyl group,
$R_2$ is a methyl group, an ethyl group or a difluoromethyl group,
$R_3$ is a hydrogen atom, a methyl group, a 3-pentyl group, a phenyl group, a 2-quinolylmethyl group or a 2-oxobenzothiazolinyl-3-ylmethyl group, and
$R_4$ is a hydrogen atom or a methyl group.

6. A pharmaceutical composition, comprising a compound according to claim 1 and a pharmaceutically acceptable carrier.

7. A method for treating tissue fibrosis, comprising administering to a patient in need thereof a compound according to claim 1.

8. A method for treating thrombosis, comprising administering to a patient in need thereof a compound according to claim 1.

* * * * *